United States Patent
Kamal et al.

(10) Patent No.: US 9,309,225 B2
(45) Date of Patent: Apr. 12, 2016

(54) N-((1-BENZYL-1H-1,2,3-TRIAZOL-4-YL)METHYL)ARYLAMIDE COMPOUNDS AS POTENTIAL ANTICANCER AGENTS AND A PROCESS FOR THE PREPARATION THEREOF

(71) Applicant: COUNCIL OF SCIENTIFIC & INDUSTRIAL RESEARCH, New Delhi (IN)

(72) Inventors: Ahmed Kamal, Hyderabad (IN); Budaganaboyina Prasad, Hyderabad (IN); Vadithe Lakshma Nayak, Hyderabad (IN); Vangala Saidi Reddy, Hyderabad (IN); Narrikolla Venkata Subba Reddy, Hyderabad (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/569,173

(22) Filed: Dec. 12, 2014

(65) Prior Publication Data
US 2015/0166507 A1 Jun. 18, 2015

(30) Foreign Application Priority Data
Dec. 16, 2013 (IN) .................. 3665/DEL/2013

(51) Int. Cl.
*C07D 401/12* (2006.01)
(52) U.S. Cl.
CPC .................. *C07D 401/12* (2013.01)
(58) Field of Classification Search
CPC .................................................. C07D 401/12
USPC ........................................ 546/268.4; 514/340
See application file for complete search history.

(56) References Cited

PUBLICATIONS

Jordan "Tamoxifen . . ." Nature Rev. v. 2, p. 205-213 (2003).*
Allan Jordan, et al., Tubulin as a Target for Anticancer Drugs: Agents Which Interact with the Mitotic Spindle, article, 1998, pp. 259-296, CCC 0198-6325/98/040259-38, John Wiley & Sons, Inc., Manchester, UK.
Mary Ann Jordan et al. , Microtubules as a Target for Anticancer Drugs, article www.nature.com/reviews/cancer, Apr. 2004, pp. 253-265, vol. 4, Nature Reviews, Santa Barbara, CA.
Koyanagi, Nozomu et al., In Vivo Tumor Growth Inhibition Produced by a NovelSulfonamide, E7010, against Rodent and Human Tumors, article, Apr. 1, 1994, pp. 1702-1706, vol. 54, Cancer Res., Japan.
Yoshino, Hirobhi, et al., Novel Sulfonamides as Potential, Systemically Active Antitumor Agents, article, Mar. 9, 1992, pp. 2496-2497, vol. 35, American Chemical Society, Ibaraki, Japan.
Yokoi, Akira, et al., Profiling Novel Sulfonamide Antitumor Agents with Cell-based Phenotypic Screens and Array-based Gene Expression Analysis, article, Feb. 2002, pp. 275-286, vol. 1, American Association for Cancer Research, Ibaraki, Japan.
Yoshimatsu, Kentaro, et al., Mechanism of Action of E7010, an Orally Active Sulfonamide Antitumor Agent: Inhibition of Mitosis by Binding to the Colchicine Site of Tubulin, article, Aug. 1, 19971, pp. 3208-3213, Vo. 57, Cancer Research, Ibaraki, Japan.
Kamal, Ahmed, et al., Synthesis and anticancer activity of chalcone-pyrrolobenzodiazepine conjugates linked via 1,2,3-triazole ring sidearmed with alkane spacers, journal, May 18, 2011, pp. 3820-3831, Elsevier Masson SAS, India.
Stefely, Jonathan A., et al., N-((1-Benzyl-1H-1,2,3-triazol-4-yl)methyl)arylamide as a New Scaffold that Provides Rapid Access to Antimicrotubule Agents: Synthesis and Evaluation of Antiproliferative Activity Against Select Cancer Cell Lines, article, Jan. 24, 2010, pp. 3389-3395, American Chemical Society, USA.

* cited by examiner

*Primary Examiner* — Patricia L Morris
(74) *Attorney, Agent, or Firm* — Banner & Witcoff, Ltd.

(57) ABSTRACT

The present invention provides a compound of general formula 1, useful as potential anticancer agents against human cancer cell lines and process for the preparation thereof.

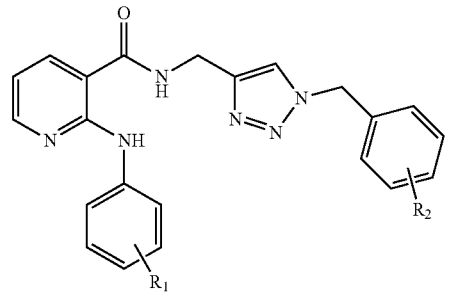

Formula 1

$R_1$=H, 4-F, 4-Cl, 4-Br, 4-OMe, 3-F, 2,4-diOMe, 2,5-diOMe, 3,5-diOMe, 3,4,5-triOMe, 4-ClBn
$R_2$=3-OPh, 4-F, 4-Cl, 4-Br, 4-OMe, 3,5-diOMe.

20 Claims, No Drawings

N-((1-BENZYL-1H-1,2,3-TRIAZOL-4-YL) METHYL)ARYLAMIDE COMPOUNDS AS POTENTIAL ANTICANCER AGENTS AND A PROCESS FOR THE PREPARATION THEREOF

CROSS-REFERENCE TO RELATED APPLICATION

This application claims priority to and is a non-provisional of Indian Provisional Application No. 3665/DEL/2013, filed on Dec. 16, 2013, which application is incorporated by reference herein in its entirety.

FIELD OF THE INVENTION

The present invention relates to N-((1-Benzyl-1H-1,2,3-triazol-4-yl)methyl)arylamides as anticancer agents and process for the preparation thereof. The present invention particularly relates to N-((1-benzyl-1H-1,2,3-triazol-4-yl)methyl)arylamides of formula 1.

Formula 1

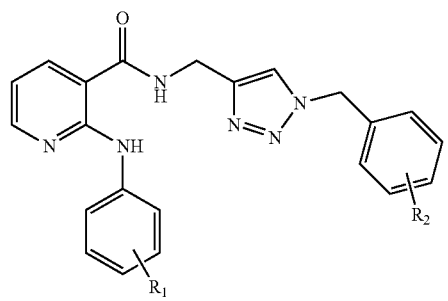

$R_1$ = H, 4-F, 4-Cl, 4-Br, 4-OMe, 3-F, 2,4-diOMe, 2,5-diOMe, 3,5-diOMe, 3,4,5-triOMe, 4-ClBn
$R_2$ = 3-OPh, 4-F, 4-Cl, 4-Br, 4-OMe, 3,5-diOMe

BACKGROUND OF THE INVENTION

Small molecules which affect the tubulin polymerization have attracted much attention in chemistry, biology, and particularly in medicine fields for the past few years. One of the recognized targets in cancer research is represented by microtubules (Tubulin as a Target for Anticancer Drugs: Agents which Interact with the Mitotic Spindle. Jordan, A.; Hadfield, J. A.; Lawrence, N. J.; McGown, A. T. *Med. Res. Rev.* 1998, 18, 259-296.). Microtubule-targeting agents (taxanes and vinca alkaloids) have played a crucial role in the treatment of diverse human cancers (Microtubules as a Target for Anticancer Drugs. Jordan, M. A.; Wilson, L. *Nat. Rev. Cancer* 2004, 4, 253-265). However, they have certain limitations in their clinical utility, such as drug resistance, high systemic toxicity, complex syntheses, and isolation procedure. Therefore, identification of new molecules with tubulin binding mechanism is attractive for the discovery and development of novel anticancer agents.

E7010, (Novel sulfonamides as potential, systemically active antitumor agents. Yoshino, H.; Ueda, N.; Niijima, J.; Sugumi, H.; Kotake, Y.; Koyanagi, N.; Yoshimatsu, K.; Asada, M.; Watanabe, T.; Nagasu, T. *J. Med. Chem.* 1992, 35, 2496-2497) a sulphonamide exhibits good antitumor activity by inhibiting tubulin polymerization, (In vivo tumor growth inhibition produced by a novel sulfonamide, E7010, against rodent and human tumors Koyanagi, N.; Nagasu, T.; Fujita, F.; Watanabe, T.; Tsukahara, K.; Funahashi, Y.; Fujita, M.; Taguchi, Yoshino, H.; Kitoh, K. *Cancer Res.* 1994, 54, 1702-1706.), which causes cell cycle arrest and apoptosis in M phase (Yokoi, A.; Kuromitsu, J.; Kawai, T.; Nagasu, T.; Sugi, N. H.; Yoshimatsu, K.; Yoshino, H.; Owa, T. *Mol. Cancer Ther.* 2002, 1, 275-286; Mechanism of action of E7010, an orally active sulfonamide antitumor agent: inhibition of mitosis by binding to the colchicine site of tubulin. Yoshimatsu, K.; Yamaguchi, A.; Yoshino, H.; Koyanagi, N.; Kitoh, K. *Cancer Res.* 1997, 57, 3208-3213.).

Structure of E7010

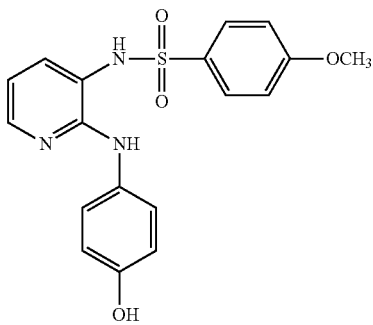

1,2,3-triazole moieties have displayed a broad range of biological properties such as antifungal, anti-allergic, antibacterial, anti-HIV, anticonvulsant, anti-inflammatory and antitubercular activities. Particularly, these triazoles exhibited anticancer activity (Synthesis and anticancer activity of chalcone-pyrrolobenzodiazepine conjugates linked via 1,2,3-triazole ring side-armed with alkane spacers. Kamal, A.; Prabhakar, S.; Ramaiah, M. J.; Reddy, P. V.; Reddy, C. R.; Mallareddy, A.; Shankaraiah, N.; Reddy, T. L. N.; Pushpavalli, S. N. C. V. L.; Bhadra, M. P. *Eur. J. Med. Chem.* 2011, 46, 3820-3831; Stefely et al. have described a limited number of 1,3-oxazole triazoles which have a limited scope of determining the antitumor activity of these of these compounds. N-((1-Benzyl-1H-1,2,3-triazol-4-yl)methyl)arylamide as a new scaffold that provides rapid access to antimicrotubule agents: Synthesis and evaluation of antiproliferative activity against select cancer cell Lines. Stefely, J. A.; Palchaudhuri, R.; Miller, P. A.; Peterson, R. J.; Moraski, G. C.; Hergenrother, P. J.; Miller, M. J. *J. Med. Chem.* 2010, 53, 3389-3395). Accordingly, there is a need of more potent antitumor agents which is solved by the present invention.

OBJECTIVES OF THE INVENTION

The main objective of the present invention is to provide novel N-((1-benzyl-1H-1,2,3-triazol-4-yl)methyl)arylamide analogues 1a-k to 6a-k useful as antitumor agents.

Yet another object of the present invention is to provide a process for the preparation of novel N-((1-benzyl-1H-1,2,3-triazol-4-yl)methyl)arylamide derivatives.

SUMMARY OF THE INVENTION

The present invention provides a compound of formula 1,

Formula 1

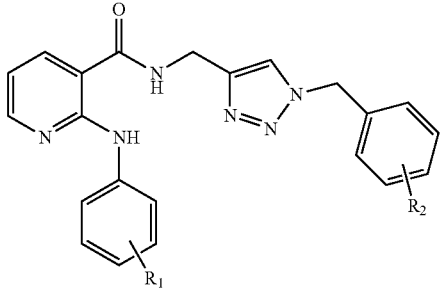

wherein R1 is optionally selected form the group comprising of hydrogen, halogen or ether and R2 is optionally selected from the group comprising of halogen or ether.

Also, the present invention provides a process for preparation of the compounds of formula 1.

DETAILED DESCRIPTION OF THE INVENTION

Accordingly, the present invention provides a compound of formula 1,

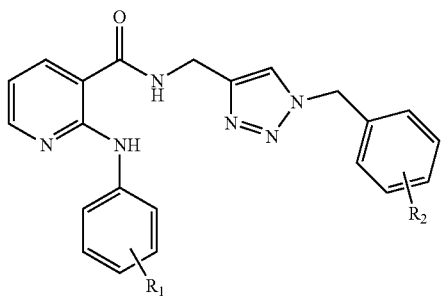

Formula 1 wherein R1 is optionally selected from the group comprising of hydrogen, halogen or ether and R2 is optionally selected from the group comprising of halogen or ether.

In an embodiment of the present invention, halogen group of R1 is selected from the group consisting of chlorine, bromine or fluorine.

In another embodiment of the present invention, ether group of R1 is selected from the group consisting of methoxy, dimethoxy or trimethoxy ether.

In one embodiment of the present invention, halogen group of R2 is selected from the group consisting of chlorine, bromine or fluorine.

In another embodiment of the present invention, ether group of R2 is selected from the group consisting of methoxy, dimethoxy, trimethoxy, or phenoxy ether.

In yet another embodiment of the present invention wherein the representative compounds comprising:

N-((1-(3-Phenoxybenzyl)-1H-1,2,3-triazol-4-yl)methyl)-2-(phenylamino)nicotinamide (1a)
2-(4-Fluorophenylamino)-N-((1-(3-phenoxybenzyl)-1H-1,2,3-triazol4-yl)methyl)nicotinamide (1b)
2-(4-Chlorophenylamino)-N-((1-(3-phenoxybenzyl)-1H-1,2,3-triazol-4-yl)methyl)nicotinamide (1c)
2-(4-Bromophenylamino)-N-((1-(3-phenoxybenzyl)-1H-1,2,3-triazol-4-yl)methyl)nicotinamide (1d)
2-(4-Methoxyphenylamino)-N-((1-(3-phenoxybenzyl)-1H-1,2,3-triazol-4-yl)methyl) nicotinamide (1e)
2-(3-Fluorophenylamino)-N-((1-(3-phenoxybenzyl)-1H-1,2,3-triazol-4-yl)methyl) nicotinamide (1f)
2-(2,4-Dimethoxyphenylamino)-N-((1-(3-phenoxybenzyl)-1H-1,2,3-triazol-4-yl)methyl) nicotinamide (1g)
2-(2,5-Dimethoxyphenylamino)-N-((1-(3-phenoxybenzyl)-1H-1,2,3-triazol-4-yl)methyl) nicotinamide (1h)
2-(3,5-Dimethoxyphenylamino)-N-((1-(3-phenoxybenzyl)-1H-1,2,3-triazol-4-yl)methyl) nicotinamide (1i)
N-((1-(3-Phenoxybenzyl)-1H-1,2,3-triazol-4-yl)methyl)-2-(3,4,5-trimethoxyphenylamino) nicotinamide (1j)
2-(4-Chlorobenzylamino)-N-((1-(3-phenoxybenzyl)-1H-1,2,3-triazol-4-yl)methyl) nicotinamide (1k)
N-((1-(4-Fluorobenzyl)-1H-1,2,3-triazol-4-yl)methyl)-2-(phenylamino)nicotinamide (2a)
N-((1-(4-Fluorobenzyl)-1H-1,2,3-triazol-4-yl)methyl)-2-((4-fluorophenyl)amino) nicotinamide (2b)
2-((4-Chlorophenyl)amino)-N-((1-(4-fluorobenzyl)-1H-1,2,3-triazol-4-yl)methyl) nicotinamide (2c)
2-((4-Bromophenyl)amino)-N-((1-(4-fluorobenzyl)-1H-1,2,3-triazol-4-yl)methyl) nicotinamide (2d)
N-((1-(4-Fluorobenzyl)-1H-1,2,3-triazol-4-yl)methyl)-2-((4-methoxyphenyl)amino) nicotinamide (2e)
N-((1-(4-Fluorobenzyl)-1H-1,2,3-triazol-4-yl)methyl)-2-((3-fluorophenyl)amino) nicotinamide (2f)
2-((2,4-Dimethoxyphenyl)amino)-N-((1-(4-fluorobenzyl)-1H-1,2,3-triazol-4-yl)methyl) nicotinamide (2g)
2-((2,5-Dimethoxyphenyl)amino)-N-((1-(4-fluorobenzyl)-1H-1,2,3-triazol-4-yl)methyl) nicotinamide (2h)
2-((3,5-Dimethoxyphenyl)amino)-N-((1-(4-fluorobenzyl)-1H-1,2,3-triazol-4-yl)methyl) nicotinamide (2i)
N-((1-(4-Fluorobenzyl)-1H-1,2,3-triazol-4-yl)methyl)-2-((3,4,5-trimethoxyphenyl)amino) nicotinamide (2j)
2-(4-Chlorobenzylamino)-N-((1-(4-fluorobenzyl)-1H-1,2,3-triazol-4-yl)methyl) nicotinamide (2k)
N-((1-(4-Chlorobenzyl)-1H-1,2,3-triazol-4-yl)methyl)-2-(phenylamino)nicotinamide (3a)
N-((1-(4-Chlorobenzyl)-1H-1,2,3-triazol-4-yl)methyl)-2-((4-fluorophenyl)amino) nicotinamide (3b)
N-((1-(4-Chlorobenzyl)-1H-1,2,3-triazol-4-yl)methyl)-2-((4-chlorophenyl)amino) nicotinamide (3c)
2-((4-Bromophenyl)amino)-N-((1-(4-chlorobenzyl)-1H-1,2,3-triazol-4-yl)methyl) nicotinamide (3d)
N-((1-(4-Bromobenzyl)-1H-1,2,3-triazol-4-yl)methyl)-2-((4-methoxyphenyl)amino) nicotinamide (3e)
N-((1-(4-Chlorobenzyl)-1H-1,2,3-triazol-4-yl)methyl)-2-((3-fluorophenyl)amino) nicotinamide (3f)
N-((1-(4-Chlorobenzyl)-1H-1,2,3-triazol-4-yl)methyl)-2-((2,4-dimethoxyphenyl)amino) nicotinamide (3g)
N-((1-(4-Chlorobenzyl)-1H-1,2,3-triazol-4-yl)methyl)-2-((2,5-dimethoxyphenyl)amino) nicotinamide (3h)
N-((1-(4-Bromobenzyl)-1H-1,2,3-triazol-4-yl)methyl)-2-((3,5-dimethoxyphenyl)amino) nicotinamide (3i)
N-((1-(4-Chlorobenzyl)-1H-1,2,3-triazol-4-yl)methyl)-2-((3,4,5-trimethoxyphenyl)amino) nicotinamide (3j)
N-((1-(4-Chlorobenzyl)-1H-1,2,3-triazol-4-yl)methyl)-2-((4-chlorobenzyl)amino) nicotinamide (3k)
N-((1-(4-Bromobenzyl)-1H-1,2,3-triazol-4-yl)methyl)-2-(phenylamino)nicotinamide (4a)
N-((1-(4-Bromobenzyl)-1H-1,2,3-triazol-4-yl)methyl)-2-((4-fluorophenyl)amino) nicotinamide (4b)
N-((1-(4-Bromobenzyl)-1H-1,2,3-triazol-4-yl)methyl)-2-((4-chlorophenyl)amino) nicotinamide (4c)
N-((1-(4-Bromobenzyl)-1H-1,2,3-triazol-4-yl)methyl)-2-((4-bromophenyl)amino) nicotinamide (4d)
N-((1-(4-Bromobenzyl)-1H-1,2,3-triazol-4-yl)methyl)-2-((4-methoxyphenyl)amino) nicotinamide (4e)
N-((1-(4-Bromobenzyl)-1H-1,2,3-triazol-4-yl)methyl)-2-((3-fluorophenyl)amino) nicotinamide (4f)
N-((1-(4-Bromobenzyl)-1H-1,2,3-triazol-4-yl)methyl)-2-((2,4-dimethoxyphenyl)amino) nicotinamide (4g)
N-((1-(4-Bromobenzyl)-1H-1,2,3-triazol-4-yl)methyl)-2-((2,5-dimethoxyphenyl)amino) nicotinamide (4h)
N-((1-(4-Bromobenzyl)-1H-1,2,3-triazol-4-yl)methyl)-2-((3,5-dimethoxyphenyl)amino) nicotinamide (4i)
N-((1-(4-Bromobenzyl)-1H-1,2,3-triazol-4-yl)methyl)-2-((3,4,5-trimethoxyphenyl)amino) nicotinamide (4j)
N-((1-(4-Bromobenzyl)-1H-1,2,3-triazol-4-yl)methyl)-2-((4-chlorobenzyl)amino) nicotinamide (4k)
N-((1-(4-Methoxybenzyl)-1H-1,2,3-triazol-4-yl)methyl)-2-(phenylamino)nicotinamide (5a)

2-((4-Fluorophenyl)amino)-N-((1-(4-methoxybenzyl)-1H-1,2,3-triazol-4-yl)methyl) nicotinamide (5b)

2-((4-Chlorophenyl)amino)-N-((1-(4-methoxybenzyl)-1H-1,2,3-triazol-4-yl)methyl) nicotinamide (5c)

2-((4-Bromophenyl)amino)-N-((1-(4-methoxybenzyl)-1H-1,2,3-triazol-4-yl)methyl) nicotinamide (5d)

N-((1-(4-Methoxybenzyl)-1H-1,2,3-triazol-4-yl)methyl)-2-((4-methoxyphenyl)amino) nicotinamide (5e)

2-((3-Fluorophenyl)amino)-N-((1-(4-methoxybenzyl)-1H-1,2,3-triazol-4-yl)methyl) nicotinamide (5f)

2-((2,4-Dimethoxyphenyl)amino)-N-((1-(4-methoxybenzyl)-1H-1,2,3-triazol-4-yl)methyl) nicotinamide (5g)

2-((2,5-Dimethoxyphenyl)amino)-N-((1-(4-methoxybenzyl)-1H-1,2,3-triazol-4-yl)methyl) nicotinamide (5h)

2-((3,5-Dimethoxyphenyl)amino)-N-((1-(4-methoxybenzyl)-1H-1,2,3-triazol-4-yl)methyl) nicotinamide (5i)

N-((1-(4-Methoxybenzyl)-1H-1,2,3-triazol-4-yl)methyl)-2-((3,4,5-trimethoxyphenyl)amino) nicotinamide (5j)

N-((1-(4-Methoxybenzyl)-1H-1,2,3-triazol-4-yl)methyl)-2-((3,4,5-trimethoxyphenyl)amino) nicotinamide (5k)

N-((1-(3,5-Dimethoxybenzyl)-1H-1,2,3-triazol-4-yl)methyl)-2-(phenylamino)nicotinamide (6a)

N-((1-(3,5-Dimethoxybenzyl)-1H-1,2,3-triazol-4-yl)methyl)-2-((4-fluorophenyl)amino) nicotinamide (6b)

2-((4-Chlorophenyl)amino)-N-((1-(3,5-dimethoxybenzyl)-1H-1,2,3-triazol-4-yl)methyl) nicotinamide (6c)

2-((4-Bromophenyl)amino)-N-((1-(3,5-dimethoxybenzyl)-1H-1,2,3-triazol-4-yl)methyl) nicotinamide (6d)

N-((1-(3,5-Dimethoxybenzyl)-1H-1,2,3-triazol-4-yl)methyl)-2-((4-methoxyphenyl)amino) nicotinamide (6e)

N-((1-(3,5-Dimethoxybenzyl)-1H-1,2,3-triazol-4-yl)methyl)-2-((3-fluorophenyl)amino) nicotinamide (6f)

N-((1-(3,5-Dimethoxybenzyl)-1H-1,2,3-triazol-4-yl)methyl)-2-((2,4-dimethoxyphenyl)amino)nicotinamide (6g)

N-((1-(3,5-Dimethoxybenzyl)-1H-1,2,3-triazol-4-yl)methyl)-2-((2,5-dimethoxyphenyl)amino) nicotinamide (6h)

N-((1-(3,5-Dimethoxybenzyl)-1H-1,2,3-triazol-4-yl)methyl)-2-((3,5-dimethoxyphenyl)amino) nicotinamide (6i)

N-((1-(3,5-Dimethoxybenzyl)-1H-1,2,3-triazol-4-yl)methyl)-2-((3,4,5-trimethoxyphenyl)amino) nicotinamide (6j)

2-((4-Chlorobenzyl)amino)-N-((1-(3,5-dimethoxybenzyl)-1H-1,2,3-triazol-4-yl)methyl) nicotinamide (6k).

In still another embodiment of the present invention, wherein the structural formula of the representative compounds comprising:

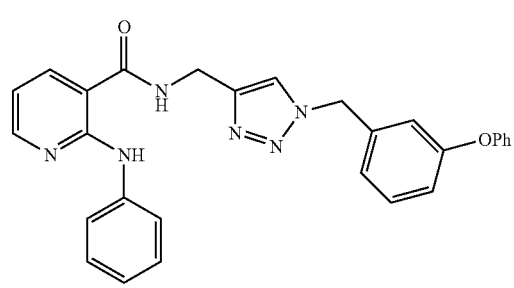

1a

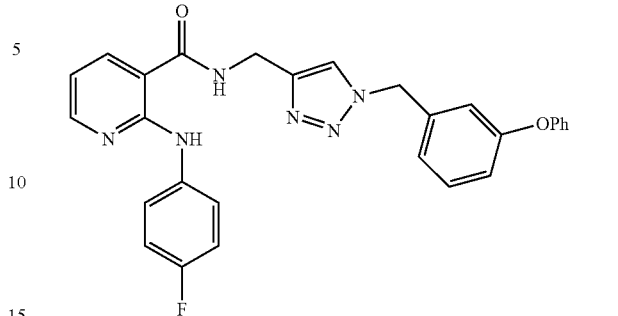

1b

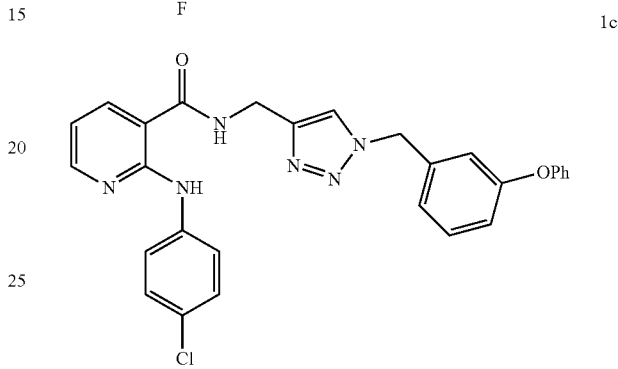

1c

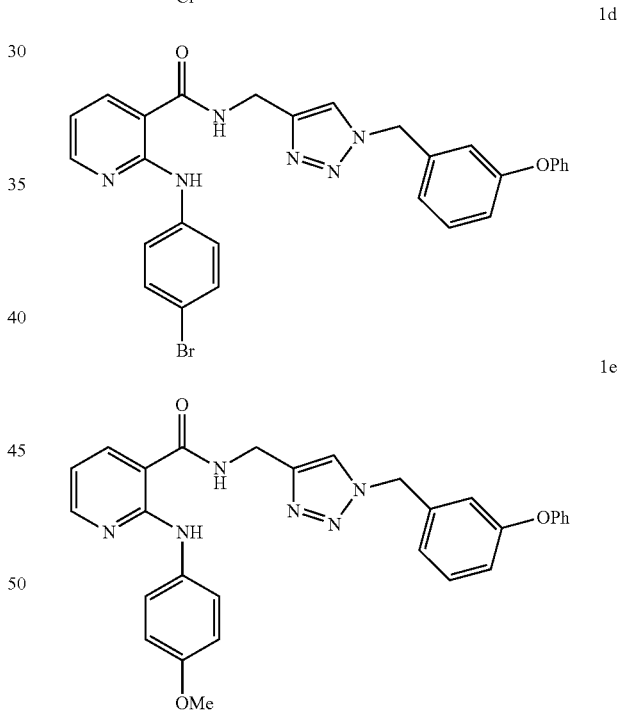

1d

1e

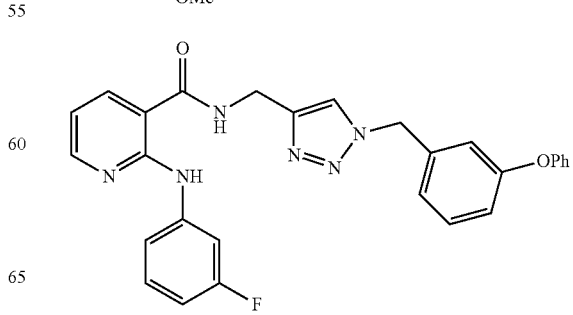

1f

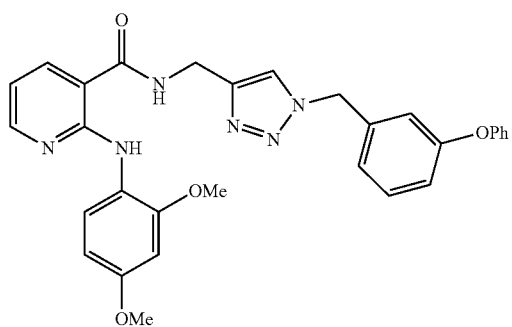
1g
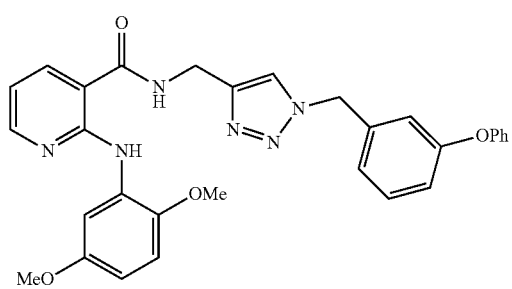
1h
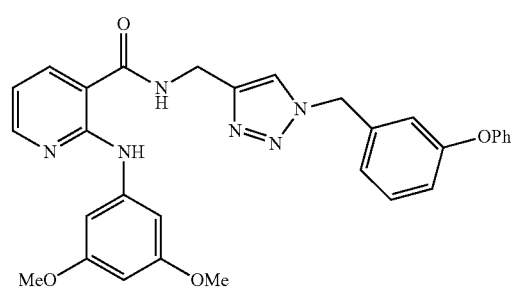
1i
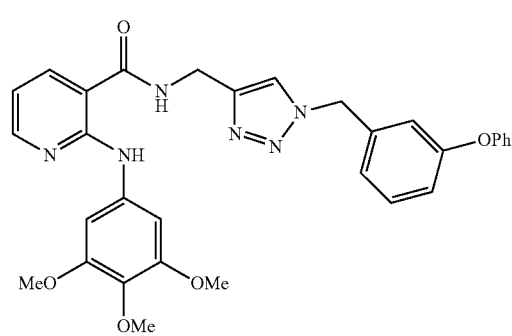
1j
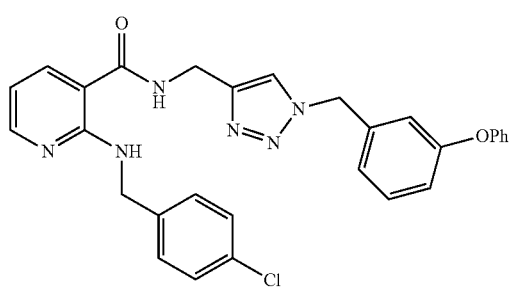
1k
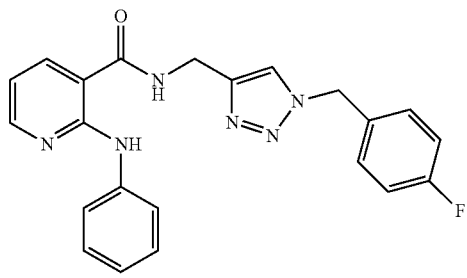
2a
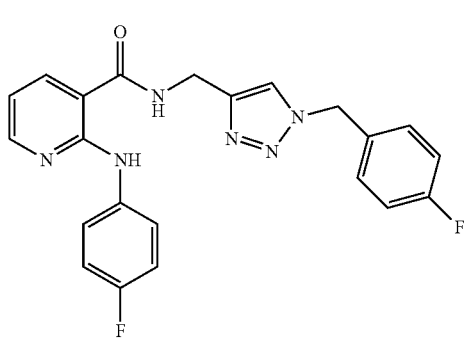
2b
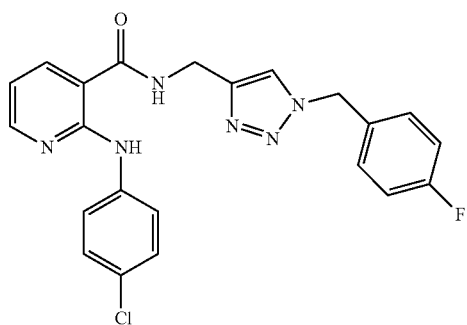
2c
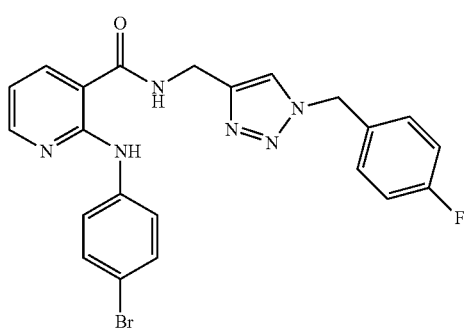
2d
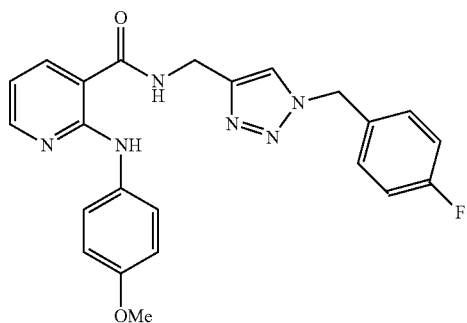
2e -continued
2f
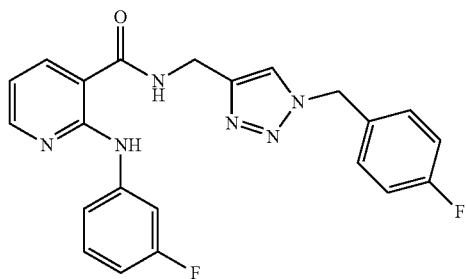
2g
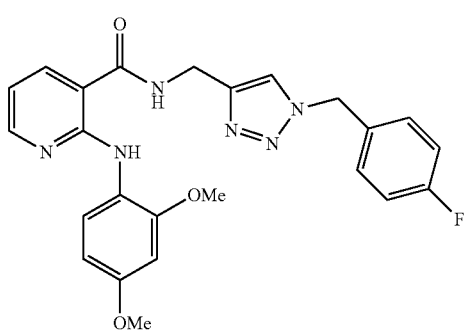
2h
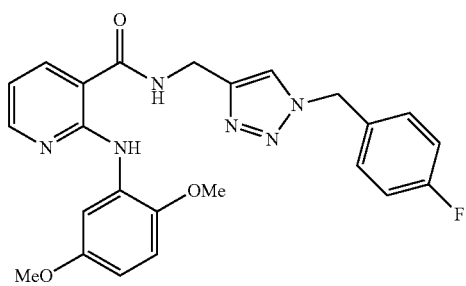
2i
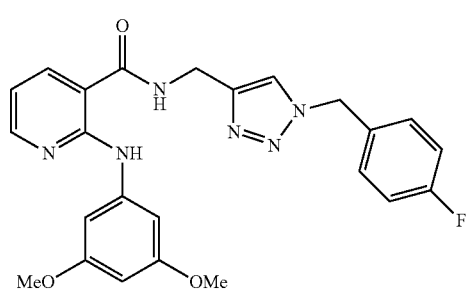
2j
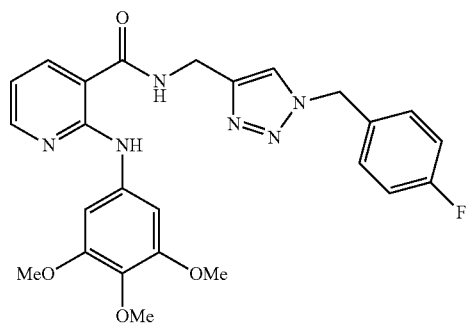
-continued
2k
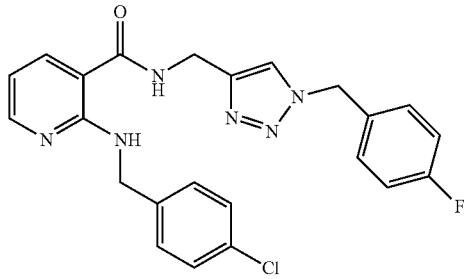
3a
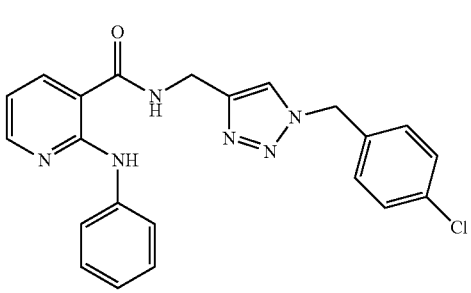
3b
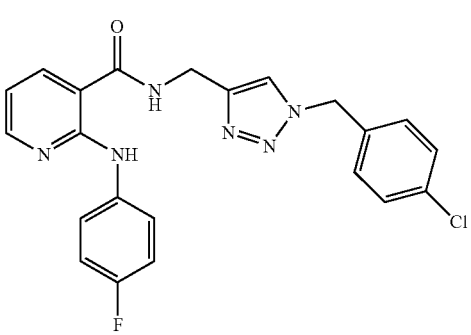
3c
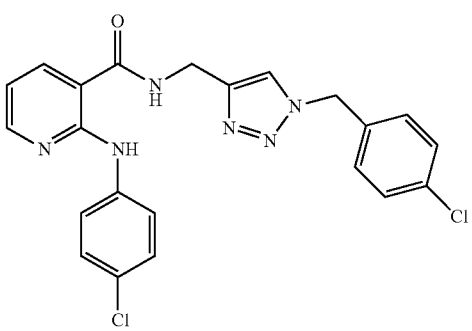
3d
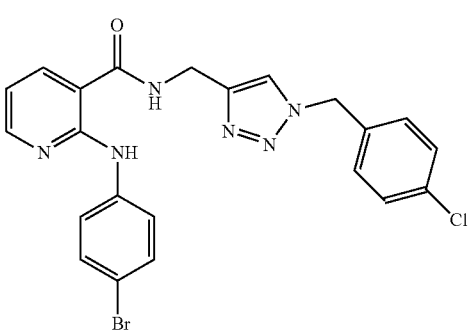

3e 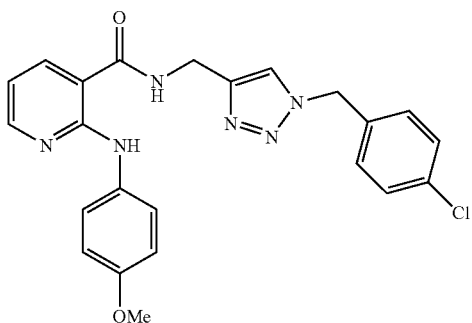
3f 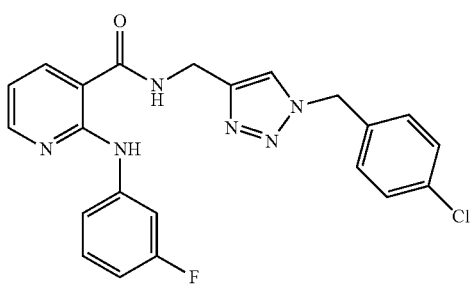
3g 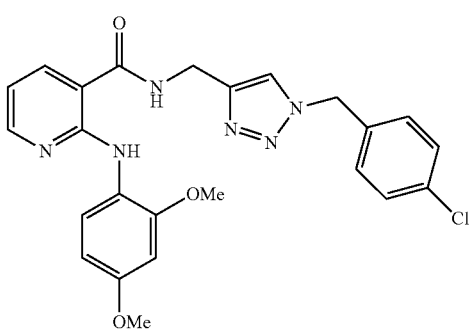
3h 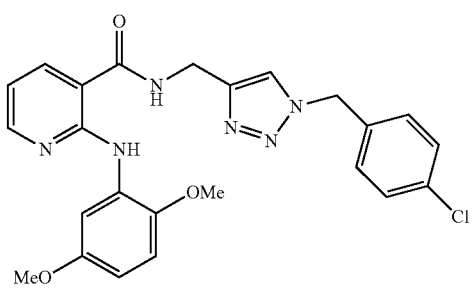
3i 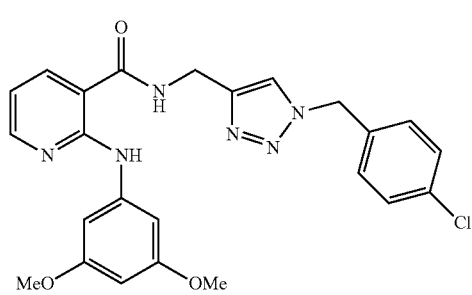
3j 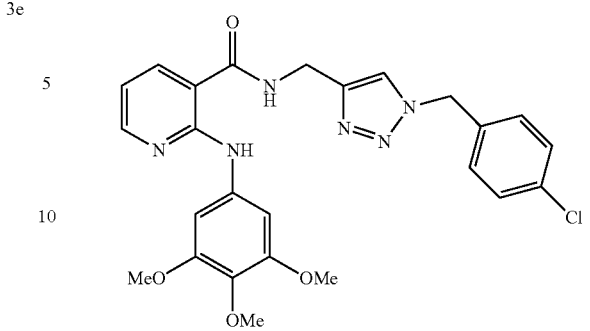
3k 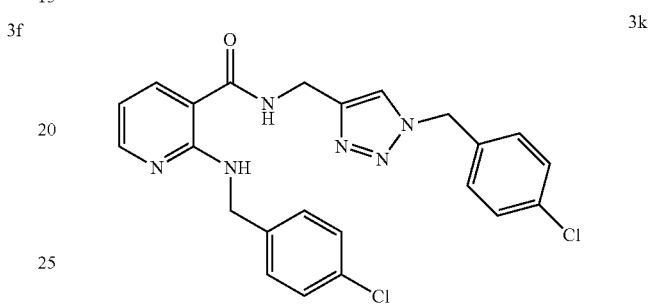
4a 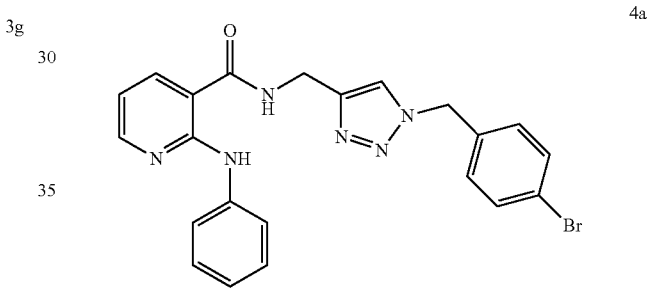
4b 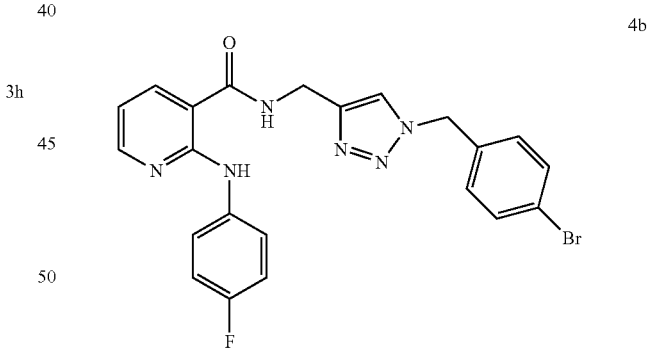
4c 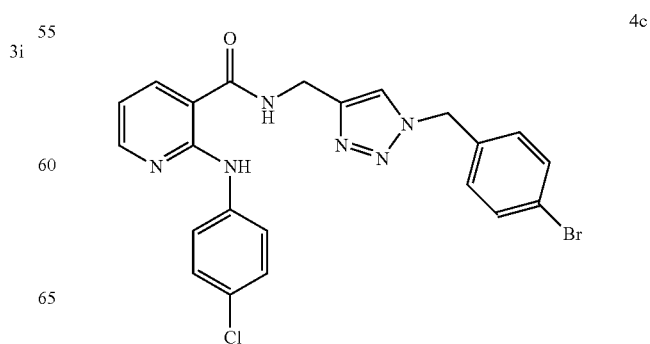

4d
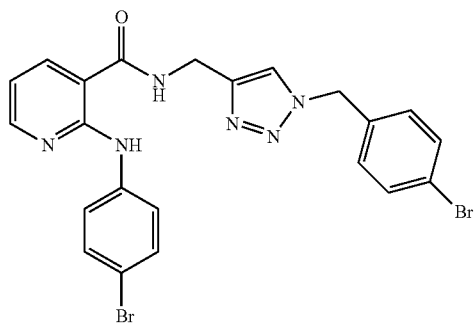
4e
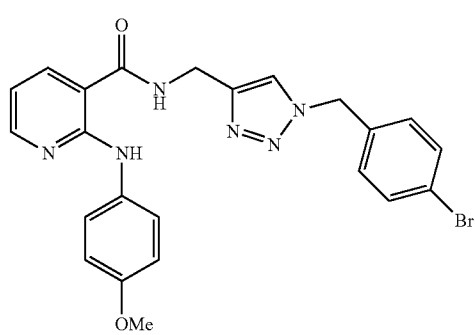
4f
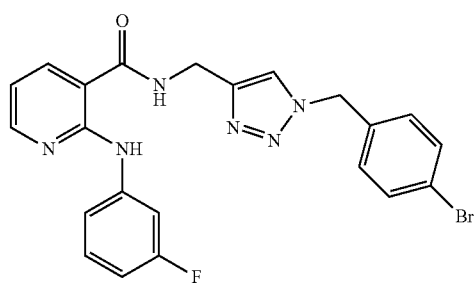
4g
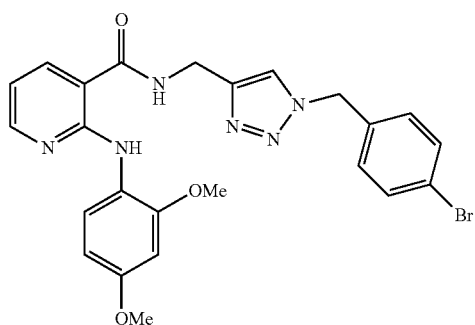
4h
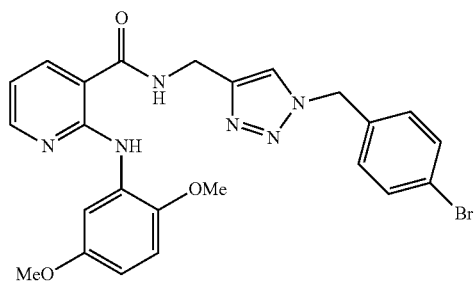
4i
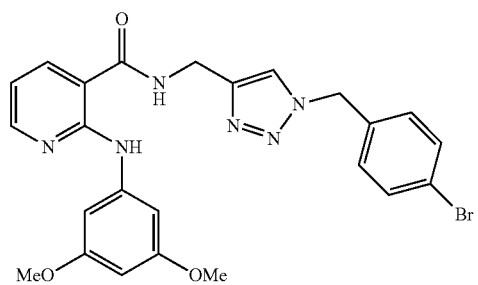
4j
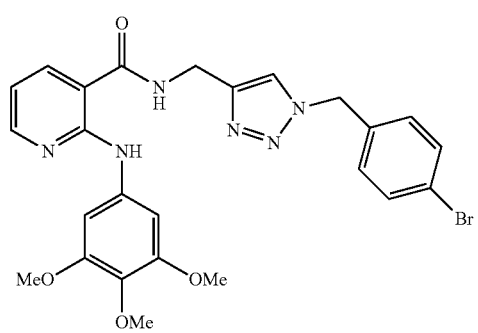
4k
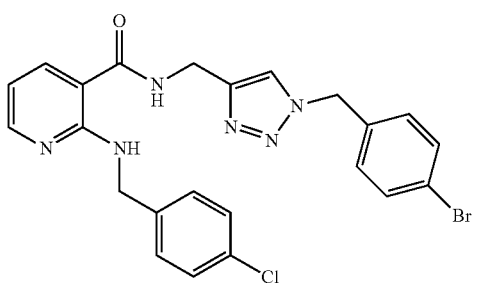
5a
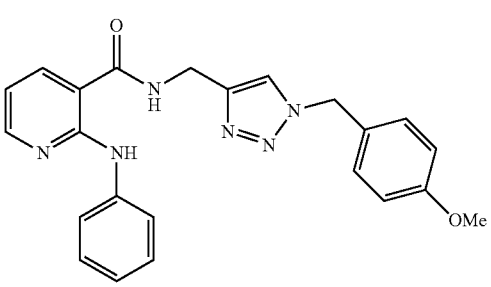
5b
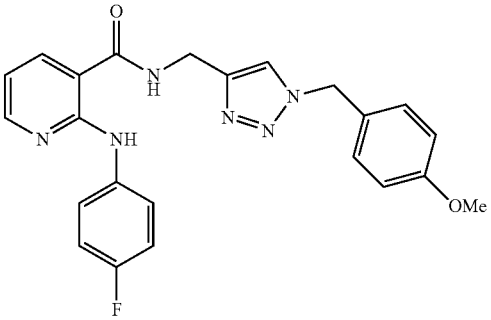

5c
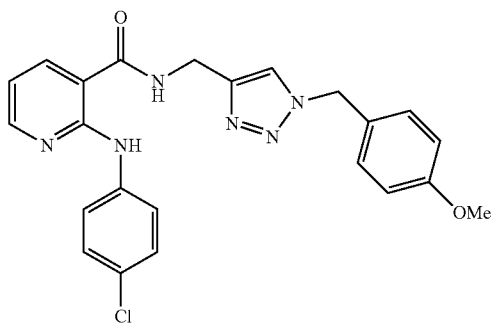
5d
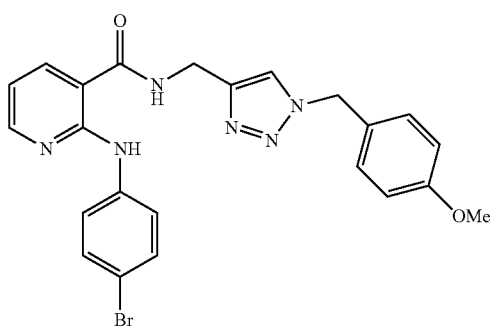
5e
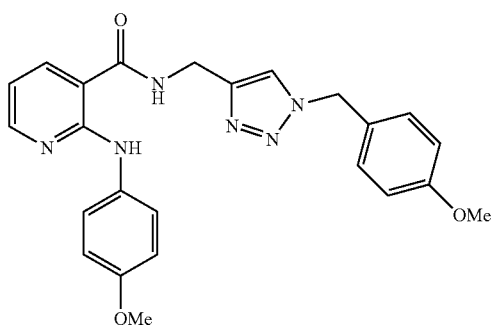
5f
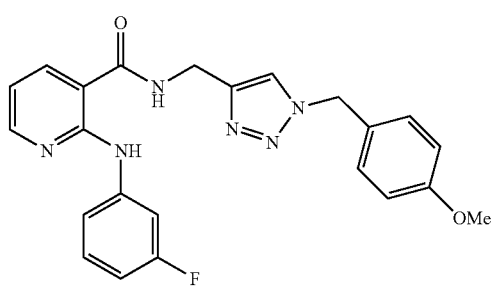
5g
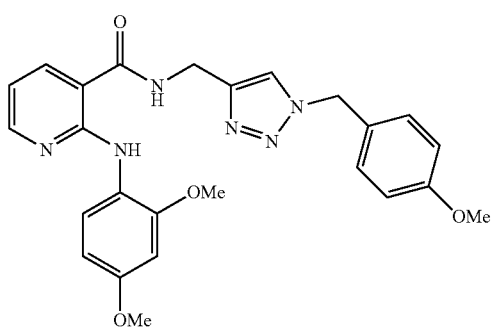
5h
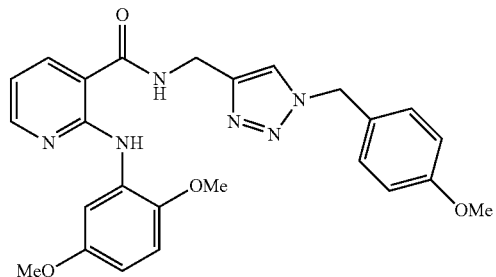
5i
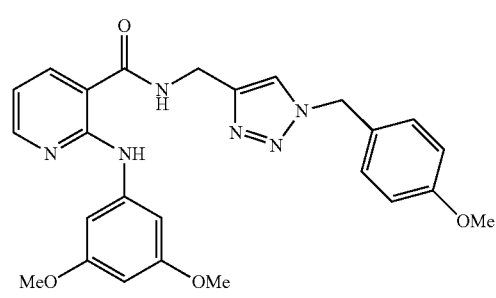
5j
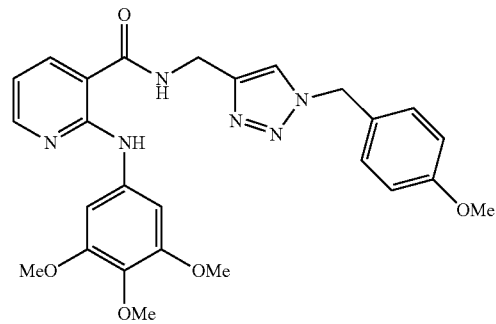
5k
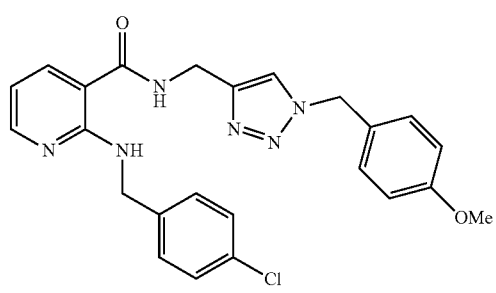
6a
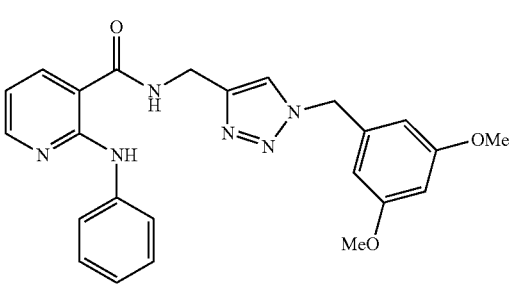

-continued

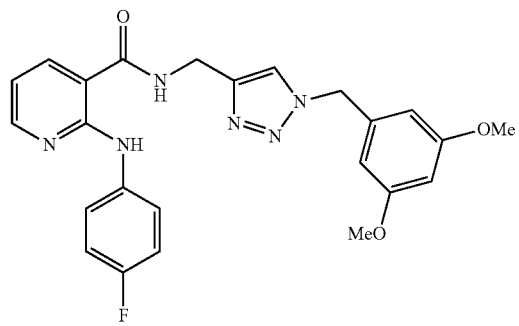
6b

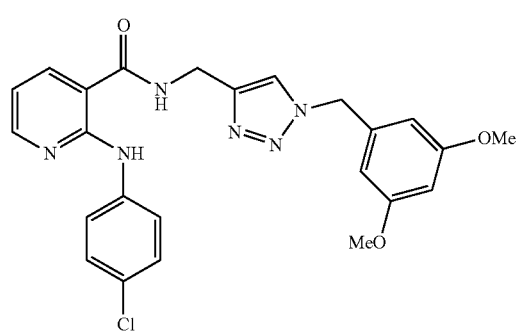
6c

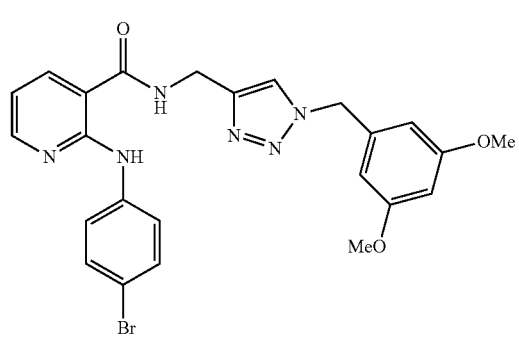
6d

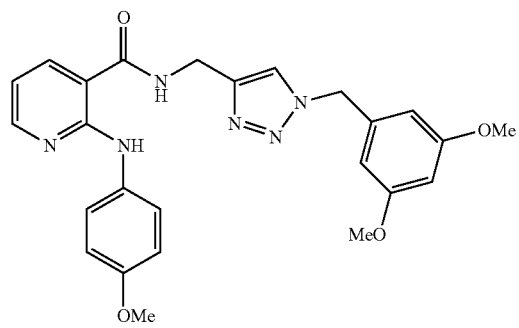
6e

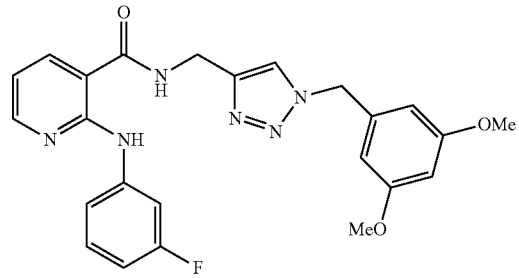
6f

-continued

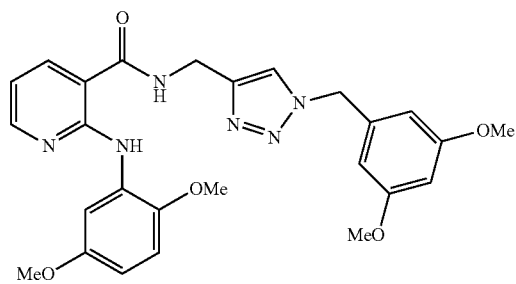
6g

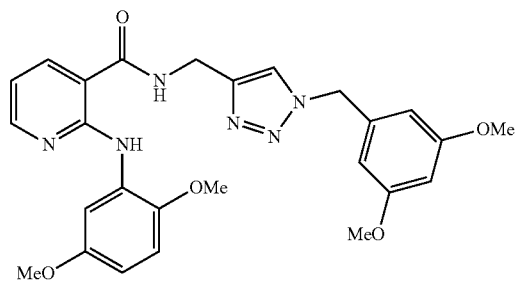
6h

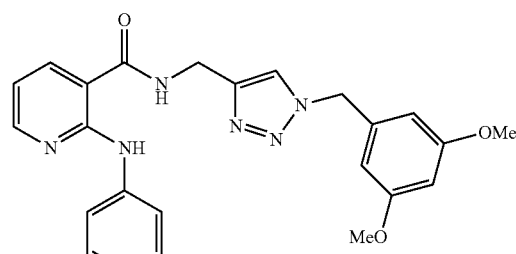
6i

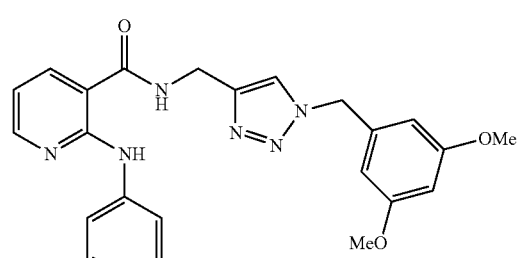
6j

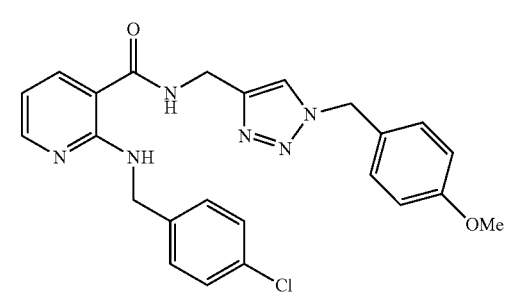
6k

In one more embodiment of the present invention, the compounds of formula 1 is useful as antitumour agents.

Accordingly, the present invention also provides a process for preparation of compounds of formula 1, wherein the process steps comprising:

i. reacting compound of formula 8 with compound of formula 9a-k in ethylene glycol at a temperature ranging between 130-140° C. for the a time period ranging between 5-6 hr to obtain substituted nicotinamide of formula 10 a-k,

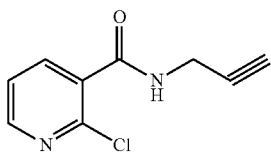

ii. reacting substituted nicotinamide of formula 10a-k as obtained in step (i) with substituted azides of formula 12a-k in a mixture of water and tert-butyl alcohol in the ratio of 2:1 followed by sequential addition of sodium ascorbate and copper sulphate at a temperature ranging between 25-30° C. for a time period ranging between 10-12 h to obtain compound of formula 1,

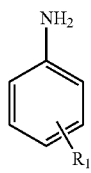

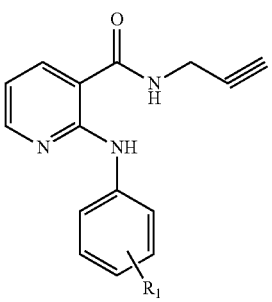

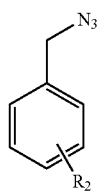

In an embodiment of the present invention wherein the compound 9 used in step (i) is selected from the group consisting of aniline, 4-fluoroaniline, 4-bromoaniline, 4 methoxyaniline, 3-fluoroaniline, 2,4-dimethoxyaniline, 2,5-dimethoxyaniline, 3,5-dimethoxyaniline, 3,4,5-trimethoxyaniline and (4-chlorophenyl)methanamine.

In another embodiment of the present invention wherein the substituted nicotinamide of formula 10 a-k used in step (ii) is selected from the group consisting of 2-(phenylamino)-N-(prop-2-ynyl)nicotinamide, 2-(4-fluorophenylamino)-N-(prop-2-ynyl)nicotinamide, 2-(4-chlorophenylamino)-N-(prop-2-ynyl)nicotinamide, 2-(4-bromophenylamino)-N-(prop-2-ynyl)nicotinamide, 2-(4-methoxyphenylamino)-N-(prop-2-ynyl)nicotinamide, 2-(3-fluorophenylamino)-N-(prop-2-ynyl)nicotinamide, 2-(2,4-dimethoxyphenylamino)-N-(prop-2-ynyl)nicotinamide, 2-(2,5-dimethoxyphenylamino)-N-(prop-2-ynyl)nicotinamide, 2-(3,5-dimethoxyphenylamino)-N-(prop-2-ynyl)nicotinamide, N-(prop-2-ynyl)-2-(3,4,5-trimethoxyphenylamino) nicotinamide and 2-(4-chlorobenzylamino)-N-(prop-2-ynyl) nicotinamide.

In yet another embodiment of the present invention, wherein the substituted benzylazide of formula 12 a-k used in step (ii) is selected from the group consisting of 1-(azidomethyl)-3-phenoxybenzene, 1-(azidomethyl)-4-fluorobenzene, 1-(azidomethyl)-4-chlorobenzene, 1-(azidomethyl)-4-bromobenzene, 1-(azidomethyl)-4-methoxybenzene and 1-(azidomethyl)-3,5-dimethoxybenzene.

The precursor substituted anilines (9a-k) and substituted benzyl alcohols are commercially available and the N-((1-benzyl-1H-1,2,3-triazol-4-yl)methyl) arylamides of formulae 1a-k to 6a-k have been prepared as illustrated in the Scheme.

i) To the solution of 2-choronicotinic acid (5 g, 31.84 mmol) in dry DCM under nitrogen, Oxalyl chloride (38.21 mmol) and catalytic amount of N,N-dimethylformamide were added carefully with stirring. The reaction was stirred for 3 hr. The solution was concentrated under vacuum to yield 2-chloronicotinyl chloride as solid which was used for next reaction without purification.

Acid chloride (4.5 g, 25.56 mmol) was dissolved in dry DCM, cooled to 0° C., propargylamine hydrochloride (30.61 mmol) and triethylamine (76.68 mmol) were added. The reaction was warmed to room temperature. After stirring overnight, the reaction mixture was diluted with water and extracted with DCM. The organic layer was separated, washed with aq. NaHCO$_3$ and brine dried with Na$_2$SO$_4$ and concentrated in vacuum to give 8.

ii) 2-Chloro-N-(prop-2-ynyl)nicotinamide (8, 1.03 mmol) was dissolved in ethylene glycol, and treated with an appropriate aniline (9, 1.03 mmol). The reaction mixture was heated to 120-130° C. for 6 h. After the reaction was completed, the reaction mixture was diluted with water and extracted with ethylacetate. The combined extracts were dried with Na$_2$SO$_4$ and concentrated. the crude was purified by column chromatography to give pure product 10a-k as solid.

Procedure for Triazole Formation:

To a solution of corresponding aminonicotinamides (1 equivalent) and corresponding benzylazides (1 equivalent) in 2:1 mixture of water and tert-butyl alcohol, sodium ascorbate (0.1 equivalents) and copper (II) sulphate (0.05 equivalents) were added sequentially. The reaction was stirred at room temperature for 10-12 h, TLC analysis indicated completion of reaction. The reaction mixture was concentrated under vacuum and extracted with EtOAc to give crude product. The crude was purified by column chromatography by ethyl acetate/petroleum ether to afford pure product.

All the N-((1-benzyl-1H-1,2,3-triazol-4-yl)methyl) arylamide derivatives were synthesized and purified by column chromatography using different solvents like ethyl acetate, hexane.

These new analogues of N-((1-benzyl-1H-1,2,3-triazol-4-yl)methyl)arylamides have shown promising anticancer activity in various cancer cell lines.

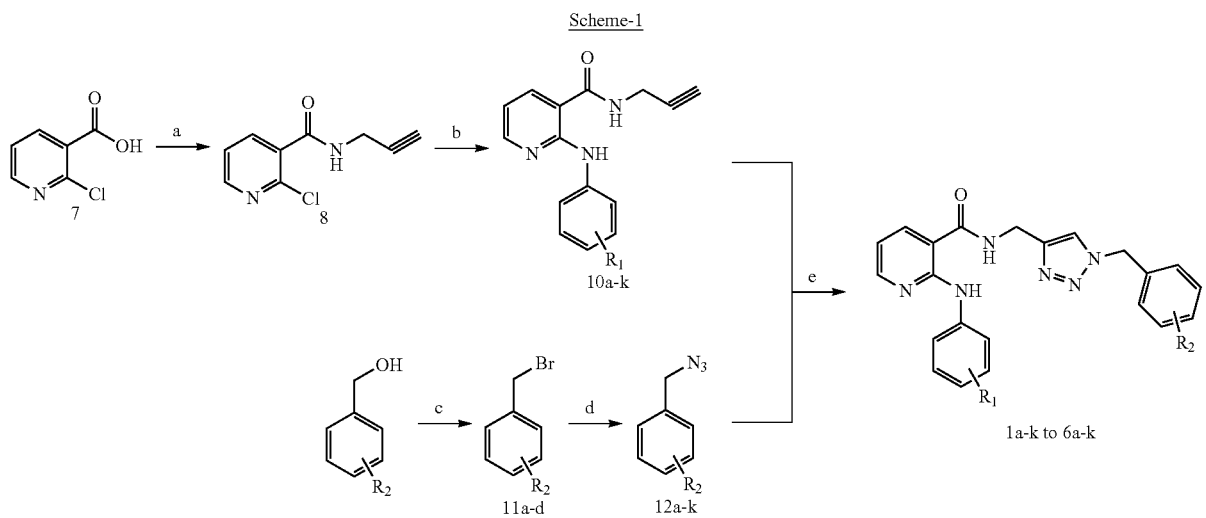

Scheme-1

Reagents and conditions:
(a) (i) oxalyl chloride, CH$_2$Cl$_2$, DMF, (ii) propargylamine hydro chloride, CH$_2$Cl$_2$, Et$_3$N;
(b) substituted anilines (9a-k), ethylene glycol, 120° C.;
(c) PBr$_3$, Ether, 0° C.;
(d) NaN$_3$ DMSO;
(e) Na Ascorbate (10 mol %), CuSO$_4$ (5 mol %), H$_2$O/t-buOH, 2:1.

EXAMPLES

The following examples are given by way of illustration of the working of the invention in actual practice and therefore should not be construed to limit the scope of present invention.

Compounds 12a-k are prepared by using the synthesis described in *J. Med. Chem.* 2010, 53, 3389-3395.

Example 1

N-((1-(3-Phenoxybenzyl)-1H-1,2,3-triazol-4-yl)methyl)-2-(phenylamino)nicotinamide(1a)

Compound 8 (194 mg, 1 mmol) and aniline (9a, 93 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(phenylamino)-N-(prop-2-ynyl)nicotinamide 10a as pure product. To a solution of 2-(phenylamino)-N-(prop-2-ynyl)nicotinamide (10a, 150 mg, 0.59 mmol) and 1-(azidomethyl)-3-phenoxybenzene (12a, 147 mg, 0.65 mmol) in 2:1 mixture of water and tert-butyl alcohol, sodium ascorbate (0.06 mmol) and copper (II) sulphate (0.005 mmol) were added sequentially. The reaction was stirred at room temperature for 10 h, TLC analysis indicated completion of reaction. The reaction mixture was concentrated under vacuum and extracted with EtOAc to give crude product. The crude was purified by column chromatography to afford pure product as solid (210 mg, 74%); mp: 124-126° C.; $^1$H NMR (300 MHz, CDCl$_3$) δ 10.51 (s, 1H), 8.25 (dd, J=2.2, 1.5 Hz, 1H), 7.84 (dd, J=2.2, 1.5 Hz, 1H), 7.80 (brs, 1H), 7.66-7.60 (m, 3H), 7.08 (t, J=7.5 Hz, 1H), 7.00-6.90 (m, 7H), 6.61-6.59 (m, 1H), 5.45 (s, 2H), 4.62 ppm (d, J=5.2 Hz, 2H); MS (ESI m/z): 477 [M+H]$^+$. Yield: 74%

Example 2

2-(4-Fluorophenylamino)-N-((1-(3-phenoxybenzyl)-1H-1,2,3-triazol4-yl)methyl)nicotinamide (1b)

Compound 8 (194 mg, 1 mmol) and 4-fluoroaniline (9b, 111 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(4-fluorophenylamino)-N-(prop-2-ynyl)nicotinamide 10b as pure product. To a solution of 2-(4-fluorophenylamino)-N-(prop-2-ynyl)nicotinamide (10b, 150 mg, 0.55 mmol) and 1-(azidomethyl)-3-phenoxybenzene (12a, 138 mg, 0.61 mmol) in 2:1 mixture of water and tert-butyl alcohol, sodium ascorbate (0.06 mmol) and copper (II) sulphate (0.005 mmol) were added sequentially. The reaction was stirred at room temperature for 11 h, TLC analysis indicated completion of reaction. The reaction mixture was concentrated under vacuum and extracted with EtOAc to give crude product. The crude was purified by column chromatography to afford pure product 1b (220 mg 80%); mp: 160-162° C.; $^1$H NMR (300 MHz, CDCl$_3$) δ 10.36 (s, 1H), 8.25 (dd, J=3.0, 1.5 Hz, 1H), 7.59 (m, 2H), 7.54 (s, 1H), 7.35-7.28 (m, 3H), 7.22 (brs, 1H), 7.11 (t, J=7.5 Hz, 1H), 7.03-6.94 (m, 7H), 6.67-6.63 (m, 1H), 5.45 (s, 2H), 4.64 ppm (d, J=6.0 Hz, 1H); MS (ESI m/z): 495 [M+H]$^+$. Yield: 80%

Example 3

2-(4-Chlorophenylamino)-N-((1-(3-phenoxybenzyl)-1H-1,2,3-triazol-4-yl)methyl)nicotinamide (1c)

Compound 8 (194 mg, 1 mmol) and 4-chloroaniline (9c, 127 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(4-chlorophenylamino)-N-(prop-2-ynyl)nicotinamide 10c as pure product. To a solution of 2-(4-chlorophenylamino)-N-(prop-2-ynyl)nicotinamide (10c 150 mg, 0.52 mmol) and 1-(azidomethyl)-3-phenoxybenzene (12c, 130 mg, 0.57 mmol) in 2:1 mixture of water and tert-butyl alcohol, sodium ascorbate (0.06 mmol) and copper (II) sulphate (0.005 mmol) were added sequentially. The reaction was stirred at room temperature for 10 h, TLC analysis indicated completion of reaction. The reaction mixture was concentrated under vacuum and extracted with EtOAc to give crude product. The crude was purified by column chromatography to afford pure product 1c (204 mg 76%); mp: 127-129° C.; $^1$H NMR (300 MHz, CDCl$_3$) δ 10.51 (s, 1H), 8.25 (dd, J=2.2, 1.5 Hz, 1H), 7.84 (dd, J=2.2, 1.5 Hz, 1H), 7.80 (brs, 1H), 7.61-7.58 (m, 3H), 7.35-7.23 (m, 4H), 7.08 (t, J=7.5 Hz, 1H), 6.98-6.91 (m, 7H), 6.67-6.63 (m, 1H), 5.45 (s, 2H), 4.62 (d, J=5.2 Hz, 2H); MS (ESI m/z): 511 [M+H]$^+$. Yield: 76%

Example 4

2-(4-Bromophenylamino)-N-((1-(3-phenoxybenzyl)-1H-1,2,3-triazol-4-yl)methyl)nicotinamide (1d)

Compound 8 (194 mg, 1 mmol) and 4-bromoaniline (9d, 172 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(4-bromophenylamino)-N-(prop-2-ynyl)nicotinamide 10d as pure product. To a solution of 2-(4-bromophenylamino)-N-(prop-2-ynyl)nicotinamide (10d, 150 mg, 0.45 mmol) and 1-(azidomethyl)-3-phenoxybenzene (12a, 112 mg, 0.5 mmol) in 2:1 mixture of water and tert-butyl alcohol, sodium ascorbate (0.06 mmol) and copper (II) sulphate (0.005 mmol) were added sequentially. The reaction was stirred at room temperature for 11 h, TLC analysis indicated completion of reaction. The reaction mixture was concentrated under vacuum and extracted with EtOAc to give crude product. The crude was purified by column chromatography to afford pure product 1d (220 mg 80%); mp: 160-162° C.; $^1$H NMR (300 MHz, CDCl$_3$) δ 10.36 (s, 1H), 8.25 (dd, J=3.0, 1.5 Hz, 1H), 7.59 (m, 2H), 7.54 (s, 1H), 7.35-7.28 (m, 3H), 7.22 (brs, 1H), 7.11 (t, J=7.5 Hz, 1H), 7.03-6.94 (m, 7H), 6.67-6.63 (m, 1H), 5.45 (s, 2H), 4.64 ppm (d, J=6.0 Hz, 1H); MS (ESI m/z): 555 [M+H]$^+$. Yield: 80%

Example 5

2-(4-Methoxyphenylamino)-N-((1-(3-phenoxybenzyl)-1H-1,2,3-triazol-4-yl)methyl) nicotinamide (1e)

Compound 8 (194 mg, 1 mmol) and 4-methoxyaniline (9e, 123 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(4-methoxyphenylamino)-N-(prop-2-ynyl)nicotinamide 10e as pure product. To a solution of 2-(4-methoxyphenylamino)-N-(prop-2-ynyl)nicotinamide (10e, 150 mg, 0.53 mmol) and 1-(azidomethyl)-3-phenoxybenzene (12a, 132 mg, 0.58 mmol) in 2:1 mixture of water and tert-butyl alcohol, sodium ascorbate (0.06 mmol) and copper (II) sulphate (0.005 mmol) were added sequentially. The reaction was stirred at room temperature for 11 h, TLC analysis indicated completion of reaction. The reaction mixture was concentrated under vacuum and extracted with EtOAc to give crude product. The crude was purified by column chromatography to afford pure product 1f (202 mg, 75%); mp: 95-98° C.; $^1$H NMR (300 MHz, CDCl$_3$) δ 10.32 (s, 1H), 8.18 (dd, J=3.0, 1.5 Hz, 1H), 7.80 (dd, J=3.0, 1.5 Hz, 2H), 7.59 (s, 1H), 7.49 (d, J=8.3 Hz, 2H), 7.33-7.27 (m, 3H), 7.07 (t, J=7.5 Hz, 1H), 6.96-6.90 (m, 5H), 6.85-6.79 (m, 2H), 6.54-6.50 (m, 1H), 5.45 (s, 2H), 4.60 (d, J=5.2 Hz, 2H) 3.78 (s, 3H); MS (ESI m/z): 507 [M+H]$^+$. Yield: 75%

Example 6

2-(3-Fluorophenylamino)-N-((1-(3-phenoxybenzyl)-1H-1,2,3-triazol-4-yl)methyl)nicotinamide (1f)

Compound 8 (194 mg, 1 mmol) and 3-fluoroaniline (9f, 111 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(3-fluorophenylamino)-N-(prop-2-ynyl)nicotinamide 10f as pure product. To a solution of 2-(3-fluorophenylamino)-N-(prop-2-ynyl)nicotinamide (10f, 150 mg, 0.55 mmol) and 1-(azidomethyl)-3-phenoxybenzene (12a, 86 mg, 0.61 mmol) in 2:1 mixture of water and tert-butyl alcohol, sodium ascorbate (0.06 mmol) and copper (II) sulphate (0.005 mmol) were added sequentially. The reaction was stirred at room temperature for 12 h, TLC analysis indicated completion of reaction. The reaction mixture was concentrated under vacuum and extracted with EtOAc to give crude product. The crude was purified by column chromatography to afford pure product 1e (220 mg, 80%); mp: 130-132° C.; $^1$H NMR (300 MHz, CDCl$_3$) δ 10.62 (s, 1H), 8.31 (dd, J=3.0, 1.7 Hz, 1H), 7.83 (dd, J=3.0, 1.7 Hz, 1H), 7.78-7.73 (m, 1H), 7.59-7.53 (m, 2H), 7.36-7.18 (m, 3H), 7.12 (t, J=7.5 Hz, 1H), 6.99-6.91 (m, 5H), 6.71-6.66 (m, 2H), 5.48 (s, 2H), 4.66 ppm (d, J=5.6 Hz, 2H); MS (ESI m/z): 495 [M+H]$^+$. Yield: 80%

Example 7

2-(2,4-Dimethoxyphenylamino)-N-((1-(3-phenoxy-benzyl)-1H-1,2,3-triazol-4-yl)methyl)nicotinamide (1g)

Compound 8 (194 mg, 1 mmol) and 2,4-dimethoxyaniline (9 g, 153 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(2,4-dimethoxyphenylamino)-N-(prop-2-ynyl) nicotinamide 10g as pure product. To a solution of 2-(2,4-dimethoxyphenylamino)-N-(prop-2-ynyl)nicotinamide (10 g, 150 mg, 0.48 mmol) and 1-(azidomethyl)-3-phenoxybenzene (12a, 119 mg, 0.53 mmol) in 2:1 mixture of water and tert-butyl alcohol, sodium ascorbate (0.06 mmol) and copper (II) sulphate (0.004 mmol) were added sequentially. The reaction was stirred at room temperature for 10 h, TLC analysis indicated completion of reaction. The reaction mixture was concentrated under vacuum and extracted with EtOAc to give crude product. The crude was purified by column chromatography to afford pure product 1g (201 mg, 78%); mp: 127-129° C.; $^1$H NMR (300 MHz, CDCl$_3$) δ 10.30 (s, 1H), 8.25-8.21 (m, 2H), 7.73 (d, J=7.5 Hz 1H), 7.56 (s, 1H), 7.35-7.28 (m, 3H), 7.11 (t, J=7.5 Hz, 1H), 6.99-6.90 (m, 5H), 6.59-6.47 (m, 3H), 5.45 (s, 2H), 4.67 (d, J=5.2 Hz, 2H), 3.87 (s, 6H), 3.79 ppm (s, 3H); MS (ESI m/z): 537 [M+H]$^+$. Yield: 78%

Example 8

2-(2,5-Dimethoxyphenylamino)-N-((1-(3-phenoxybenzyl)-1H-1,2,3-triazol-4-yl)methyl)nicotinamide (1h)

Compound 8 (194 mg, 1 mmol) and 2,5-dimethoxyaniline (9h, 153 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(2,5-dimethoxyphenylamino)-N-(prop-2-ynyl) nicotinamide 10h as pure product. To a solution of 2-(2,5-dimethoxyphenylamino)-N-(prop-2-ynyl)nicotinamide (10h, 150 mg, 0.48 mmol) and 1-(azidomethyl)-3-phenoxybenzene (119 mg, 0.53 mmol) in 2:1 mixture of water and tert-butyl alcohol, sodium ascorbate (0.06 mmol) and copper (II) sulphate (0.005 mmol) were added sequentially. The reaction was stirred at room temperature for 11 h, TLC analysis indicated completion of reaction. The reaction mixture was concentrated under vacuum and extracted with EtOAc to give crude product. The crude was purified by column chromatography to afford pure product 1h (201 mg, 78%); mp: 154-156° C.; $^1$H NMR (300 MHz, CDCl$_3$) δ 10.71 (s, 1H), 8.34 (d, J=2.2 Hz, 1H), 8.32 (dd, J=3.0, 1.5 Hz, 1H), 7.76 (dd, J=2.2, 1.5 Hz, 1H), 7.54 (s, 2H), 7.32 (d, J=7.5 Hz, 2H), 7.28 (d, J=2.2 Hz, 1H), 7.18-7.06 (m, 2H), 6.97-6.84 (m, 5H), 6.76 (d, J=8.3 Hz 1H), 6.66-6.62 (m, 1H), 6.42-6.38 (m, 1H) 6.40 (dd, J=3.0 Hz, 1H), 5.45 (s, 2H), 4.66 (d, J=5.2 Hz, 2H), 3.90 (s, 3H), 3.79 (s, 3H); MS (ESI m/z): 537 [M+H]$^+$. Yield: 78%

Example 9

2-(3,5-Dimethoxyphenylamino)-N-((1-(3-phenoxybenzyl)-1H-1,2,3-triazol-4-yl)methyl)nicotinamide (1i)

Compound 8 (194 mg, 1 mmol) and 3,5-dimethoxyaniline (91,153 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(3,5-dimethoxyphenylamino)-N-(prop-2-ynyl) nicotinamide 10i as pure product. To a solution of 2-(3,5-dimethoxyphenylamino)-N-(prop-2-ynyl)nicotinamide (101,150 mg, 0.48 mmol) and 1-(azidomethyl)-3-phenoxybenzene (12a, 119 mg, 0.53 mmol) in 2:1 mixture of water and tert-butyl alcohol, sodium ascorbate (0.06 mmol) and copper (II) sulphate (0.005 mmol) were added sequentially. The reaction was stirred at room temperature for 11 h, TLC analysis indicated completion of reaction. The reaction mixture was concentrated under vacuum and extracted with EtOAc to give crude product. The crude was purified by column chromatography to afford pure product 1i (201 mg, 78%); mp: 123-125° C.; $^1$H NMR (300 MHz, CDCl$_3$) δ 10.55 (s, 1H), 8.27 (dd, J=2.2, 1.5 Hz, 1H), 7.82 (dd, J=2.2, 1.5 Hz, 1H), 7.72 (t, J=6.0 Hz, 1H), 7.58 (s, 1H), 7.33-7.28 (m, 1H), 7.08 (t, J=7.5 Hz, 1H), 6.97-6.90 (m, 7H), 6.62-6.58 (m, 1H), 6.08 (t, J=2.2 Hz 1H), 5.46 (s, 2H), 4.61 (d, J=5.2 Hz, 2H), 3.80 ppm (s, 6H); MS (ESI m/z): 537 [M+H]$^+$ Yield: 78%

Example 10

N-((1-(3-Phenoxybenzyl)-1H-1,2,3-triazol-4-yl)methyl)-2-(3,4,5-trimethoxyphenylamino) nicotinamide (1j)

Compound 8 (194 mg, 1 mmol) and 3,4,5-trimethoxyaniline (9j, 183 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain N-(prop-2-ynyl)-2-(3,4,5-trimethoxyphenylamino) nicotinamide 10j as pure product. To a solution of N-(prop-2-ynyl)-2-(3,4,5-trimethoxyphenylamino)nicotinamide (10j, 150 mg, 0.41 mmol) and 1-(azidomethyl)-3-phenoxybenzene (12a, 102 mg, 0.45 mmol), in 2:1 mixture of water and tert-butyl alcohol, sodium ascorbate (0.06 mmol) and copper (II) sulphate (0.004 mmol) were added sequentially. The reaction was stirred at room temperature for 10 h, TLC analysis indicated completion of reaction. The reaction mixture was concentrated under vacuum and extracted with EtOAc to give crude product. The crude was purified by column chromatography to afford pure product 1j (186 mg, 75%); mp: 142-144° C.; $^1$H NMR (300 MHz, CDCl$_3$) δ 10.42 (s, 1H), 8.27 (d, J=7.5, Hz, 1H), 7.85 (d, J=7.5 Hz 2H), 7.75 (brs, 1H), 7.60 (s, 1H), 7.39-7.27 (m, 3H), 7.11 (t, J=7.5 Hz, 1H), 6.99-6.83 (m, 7H), 6.65 (m, 1H), 5.47 (s, 2H), 4.66 (d, J=5.28 Hz, 2H), 3.85 (s, 6H), 3.81 ppm (s, 3H); MS (ESI m/z): 567 [M+H]$^+$. Yield: 75%

Example 11

2-(4-Chlorobenzylamino)-N-((1-(3-phenoxybenzyl)-1H-1,2,3-triazol-4-yl)methyl) nicotinamide (1k)

Compound 8 (194 mg, 1 mmol) and 4-(4-chlorobenzyl) aniline (9k, 217 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(4-chlorobenzylamino)-N-(prop-2-ynyl)nicotinamide 10k as pure product. To a solution of 2-(4-chlorobenzylamino)-N-(prop-2-ynyl)nicotinamide (10k, 150 mg, 0.50 mmol) and 1-(azidomethyl)-3-phenoxybenzene (12a, 124 mg, 0.55 mmol) in 2:1 mixture of water and tert-butyl alcohol, sodium ascorbate (0.06 mmol) and copper (II) sulphate (0.005 mmol) were added sequentially. The reaction was stirred at room temperature for 12 h, TLC analysis indicated completion of reaction. The reaction mixture was concentrated under vacuum and extracted with EtOAc to give crude product. The crude was purified by column chromatography to afford pure product 1k (184 mg, 60%); mp: 209-211° C.; $^1$H NMR (300 MHz, CDCl$_3$) δ 8.45 (t, J=5.2 Hz, 1H), 8.14-8.11 (m, 1H), 7.63 (d, J=7.5 Hz, 1H), 7.50 (brs, 1H), 7.45 (s, 1H), 7.27-7.13 (m, 7H), 7.02 (t, J=7.5 Hz, 1H), 6.90-6.80 (m, 5H), 6.36-6.32 (m, 1H), 5.33 (s, 2H), 4.60 (d, J=5.2 Hz, 2H), 4.49 ppm (d, J=6.0 Hz, 2H); MS (ESI m/z): 525 [M+H]$^+$. Yield: 60%.

Example 12

N-((1-(4-Fluorobenzyl)-1H-1,2,3-triazol-4-yl)methyl)-2-(4-fluorophenylamino) nicotinamide (2b)

Compound 8 (194 mg, 1 mmol) and 4-fluoroaniline (9b, 111 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(4-fluorophenylamino)-N-(prop-2-ynyl)nicotinamide 10b as pure product. To a solution of 2-(4-fluorophenylamino)-N-(prop-2-ynyl)nicotinamide (10b, 150 mg, 0.55 mmol) and 1-(azidomethyl)-4-fluorobenzene (12b, 91 mg, 0.61 mmol) in 2:1 mixture of water and tert-butyl alcohol, sodium ascorbate (0.06 mmol) and copper (II) sulphate (0.005 mmol) were added sequentially. The reaction was stirred at room temperature for 10 h, TLC analysis indicated completion of reaction. The reaction mixture was concentrated under vacuum and extracted with EtOAc to give crude product. The crude was purified by column chromatography to afford pure product 2b (187 mg, 80%); mp: 197-199° C.; $^1$H NMR (300 MHz, CDCl$_3$) δ 10.61 (s, 1H), 8.63 (brs, 1H), 8.24 (dd, J=4.4, 1.4 Hz, 1H), 7.98 (dd, J=, 8.0, 1.8 Hz, 1H), 7.64 (s, 1H), 7.63-7.58 (m, 2H), 7.41 (s, 1H), 7.23 (s, 1H), 6.98 (t, J=8.4 Hz, 2H), 6.88 (t J=8.4 Hz, 2H), 6.69-6.65 (m, 1H), 5.44 (s, 2H), 4.63 (d, J=5.5 Hz, 2H), 3.78 (s, 3H); MS (ESI m/z): 421 [M+H]$^+$. Yield: 80%

Example 13

N-((1-(4-Fluorobenzyl)-1H-1,2,3-triazol-4-yl)methyl)-2-(4-methoxyphenylamino)nicotinamide (2e)

Compound 8 (194 mg, 1 mmol) and 4-methoxyaniline (9e, 123 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(4-methoxyphenylamino)-N-(prop-2-ynyl)nicotinamide 10e as pure product. To a solution of 2-(4-methoxyphenylamino)-N-(prop-2-ynyl)nicotinamide (10e, 150 mg, 0.53 mmol) and 1-(azidomethyl)-4-fluorobenzene (12b, 88 mg, 0.58 mmol) in 2:1 mixture of water and tert-butyl alcohol, sodium ascorbate (0.06 mmol) and copper (II) sulphate (0.005 mmol) were added sequentially. The reaction was stirred at room temperature for 11 h, TLC analysis indicated completion of reaction. The reaction mixture was concentrated under vacuum and extracted with EtOAc to give crude product. The crude was purified by column chromatography to afford pure product 2e (173 mg, 75%); mp: 169-171° C.; $^1$H NMR (500 MHz, CDCl$_3$) δ 10.26 (s, 1H), 8.23 (dd, J=4.0, 1.5 Hz, 1H), 7.74 (dd, J=8.0, 1.5 Hz, 1H), 7.50 (d, J=9.0 Hz, 1H), 7.29-7.24 (m, 4H), 7.06 (t, J=9.0 Hz, 2H), 6.83 (d, J=9.0 Hz, 2H), 6.59-6.50 (m, 1H), 5.47 (s, 2H), 4.64 (d, J=5.2 Hz, 2H), 3.78 (s, 3H); MS (ESI m/z): 433 [M+H]$^+$. Yield: 75%

Example 14

2-(2,4-Dimethoxyphenylamino)-N-((1-(4-fluorobenzyl)-1H-1,2,3-triazol-4-yl)methyl) nicotinamide (2g)

Compound 8 (194 mg, 1 mmol) and 2,4-dimethoxyaniline (9 g, 153 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(2,4-dimethoxyphenylamino)-N-(prop-2-ynyl) nicotinamide 10g as pure product. To a solution of 2-(2,4-dimethoxyphenylamino)-N-(prop-2-ynyl)nicotinamide (10 g, 150 mg, 0.48 mmol) and 1-(azidomethyl)-4-fluorobenzene (12b, 79 mg, 0.53 mmol) in 2:1 mixture of water and tert-butyl alcohol, sodium ascorbate (0.06 mmol) and copper (II) sulphate (0.005 mmol) were added sequentially. The reaction was stirred at room temperature for 12 h, TLC analysis indicated completion of reaction. The reaction mixture was concentrated under vacuum and extracted with EtOAc to give crude product. The crude was purified by column chromatography to afford pure product 2g (167 mg, 70%); mp: 146-148° C.; $^1$H NMR (300 MHz, CDCl$_3$) δ 10.33 (s, 1H), 8.25 (dd, J=7.5, 1.5 Hz, 1H), 7.72 (dd, J=7.5, 1.5 Hz, 1H), 7.53 (s, 1H), 7.28-7.23 (m, 3H), 7.18-7.13 (m, 1H), 7.03 (t, J=8.3 Hz, 2H), 6.58-6.54 (m, 1H), 6.46 (s, 2H), 5.45 (s, 2H), 4.64 (d, J=5.2 Hz, 2H), 3.90 (s, 3H), 3.79 (s, 3H); MS (ESI m/z): 463 [M+H]$^+$. Yield: 70%

Example 15

2-(4-Fluorophenylamino)-N-((1-(4-methoxybenzyl)-1H-1,2,3-triazol-4-yl)methyl) nicotinamide (5b)

Compound 8 (194 mg, 1 mmol) and 4-fluoroaniline (9b, 111 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(4-fluorophenylamino)-N-(prop-2-ynyl)nicotinamide 10b as pure product. To a solution of 2-(4-fluorophenylamino)-N-(prop-2-ynyl)nicotinamide (10b, 150 mg, 0.55 mmol) and 1-(azidomethyl)-4-methoxybenzene (12c, 99 mg, 0.61 mmol)) in 2:1 mixture of water and tert-butyl alcohol, sodium ascorbate (0.06 mmol) and copper (II) sulphate (0.005 mmol) were added sequentially. The reaction was stirred at room temperature for 11 h, TLC analysis indicated completion of reaction. The reaction mixture was concentrated under vacuum and extracted with EtOAc to give crude product. The crude was purified by column chromatography to afford pure product 5b (192 mg, 80%); mp: 201-204° C.; $^1$H NMR (300 MHz, CDCl$_3$) δ 10.57 (s, 1H), 8.45 (brs, 1H), 8.25 (dd, J=4.7, 1.4 Hz, 1H), 7.94 (dd, J=7.7, 1.4 Hz, 1H), 7.62-7.57 (m, 3H), 7.41 (s, 1H), 7.23 (s, 1H), 6.98 (t, J=8.4 Hz, 2H), 6.88 (t J=8.4 Hz, 2H), 6.69-6.65 (m, 1H), 5.44 (s, 2H), 4.63 (d, J=5.5 Hz, 2H), 3.78 (s, 3H); MS (ESI m/z): 433 [M+H]$^+$. Yield: 80%

Example 16

N-((1-(4-Methoxybenzyl)-1H-1,2,3-triazol-4-yl)methyl)-2-(4-methoxyphenylamino) nicotinamide (5e)

Compound 8 (194 mg, 1 mmol) and 4-methoxyaniline (9e, 123 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(4-methoxyphenylamino)-N-(prop-2-ynyl)nicotinamide 10e as pure product. To a solution of 2-(4-methoxyphenylamino)-N-(prop-2-ynyl)nicotinamide (10e, 150 mg, 0.53 mmol) and 1-(azidomethyl)-4-methoxybenzene (12c, 95 mg, 0.58 mmol) in 2:1 mixture of water and tert-butyl alcohol, sodium ascorbate (0.06 mmol) and copper (II) sulphate (0.005 mmol) were added sequentially. The reaction was stirred at room temperature for 12 h, TLC analysis indicated completion of reaction. The reaction mixture was concentrated under vacuum and extracted with EtOAc to give crude product. The crude was purified by column chromatography to afford pure product 5e (189 mg, 80%); %); $^1$H NMR (300 MHz, CDCl$_3$) δ 10.31 (s, 1H), 8.19 (dd, J=4.9, 1.7 Hz, 1H), 7.7.81 (dd, J=7.7, 1.7 Hz, 2H), 7.52-7.48 (m, 3H), 7.25-7.19 (m, 2H), 6.85-6.81 (m, 4H), 6.55-6.51 (m, 1H), 5.42 (s, 2H), 4.55 (d, J=5.4 Hz, 2H), 3.78 (s, 3H), 3.77 ppm (s, 3H); yield 80%

Example 17

2-(2,4-Dimethoxyphenylamino)-N-((1-(4-methoxybenzyl)-1H-1,2,3-triazol-4-yl)methyl) nicotinamide (5g)

Compound 8 (194 mg, 1 mmol) and 2,4-dimethoxyaniline (9e, 153 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(2,4-dimethoxyphenylamino)-N-(prop-2-ynyl) nicotinamide 10g as pure product. To a solution of 2-(2,4-dimethoxyphenylamino)-N-(prop-2-ynyl)nicotinamide (10 g, 150 mg, 0.48 mmol) and 1-(azidomethyl)-4-methoxybenzene (12c, 86 mg, 0.53 mmol) in 2:1 mixture of water and tert-butyl alcohol, sodium ascorbate (0.06 mmol) and copper (II) sulphate (0.005 mmol) were added sequentially. The reaction was stirred at room temperature for 10 h, TLC analysis indicated completion of reaction. The reaction mixture was concentrated under vacuum and extracted with EtOAc to give crude product. The crude was purified by column chromatography to afford pure product 5g (180 mg, 79%); mp: 178-180° C.; $^1$H NMR (500 MHz, CDCl$_3$) δ 10.30 (s, 1H), 8.23 (m, 2H), 7.74 (dd, J=6.0, 2.0 Hz, 2H), 7.51 (s, 1H), 7.34 (brs, 1H), 7.20 (d, J=9.0 Hz, 2H), 6.86 (d, J=9.0 Hz, 2H), 6.56-6.48 (m, 3H), 5.45 (s, 2H), 4.64 (d, J=6.0 Hz, 2H), 3.87 (s, 3H), 3.79 (s, 3H), 3.79 (s, 3H); MS (ESI m/z): 475 [M+H]$^+$. Yield: 79%

Example 18

N-((1-(3,5-Dimethoxybenzyl)-1H-1,2,3-triazol-4-yl) methyl)-2-(4-fluorophenylamino)nicotinamide (6b)

Compound 8 (194 mg, 1 mmol) and 4-fluoroaniline (9b, 111 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(4-fluorophenylamino)-N-(prop-2-ynyl)nicotinamide 10b as pure product. To a solution of from 2-(4-fluorophenylamino)-N-(prop-2-ynyl)nicotinamide (10b, 150 mg, 0.55 mmol) and 1-(azidomethyl)-3,5-dimethoxybenzene (12d, 116 mg, 0.61 mmol)) in 2:1 mixture of water and tert-butyl alcohol, sodium ascorbate (0.06 mmol) and copper (II) sulphate (0.005 mmol) were added sequentially. The reaction was stirred at room temperature for 11 h, TLC analysis indicated completion of reaction. The reaction mixture was concentrated under vacuum and extracted with EtOAc to give crude product. The crude was purified by column chromatography to afford pure product 6b (182 mg, 71%); mp: 209-211° C.; mp: 140-142° C.; $^1$H NMR (300 MHz, CDCl$_3$) δ 10.32 (s, 1H), 8.19 (dd, J=3.0, 1.5 Hz, 1H), 7.81 (dd, J=3.0, 1.5 Hz, 2H), 7.52-7.47 (m, 3H), 7.20 (d, J=9.0 Hz, 2H), 6.83 (t, J=7.5 Hz, 4H), 6.55-6.51 (m, 1H), 5.41 (s, 2H), 4.58 (d, J=4.5 Hz, 2H), 3.78 (s, 3H), 3.77 (s, 3H); MS (ESI m/z): 463 [M+H]$^+$ Yield: 71%

Example 19

N-((1-(3,5-Dimethoxybenzyl)-1H-1,2,3-triazol-4-yl) methyl)-2-(4-methoxyphenylamino) nicotinamide (6e)

Compound 8 (194 mg, 1 mmol) and 4-methoxyaniline (9e, 123 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(4-methoxyphenylamino)-N-(prop-2-ynyl)nicotinamide 10e as pure product. To a solution of 2-(4-methoxyphenylamino)-N-(prop-2-ynyl)nicotinamide (10e, 150 mg, 0.53 mmol) and 1-(azidomethyl)-3,5-dimethoxybenzene (12d, 102 mg, 0.58 mmol) in 2:1 mixture of water and tert-butyl alcohol, sodium ascorbate (0.06 mmol) and copper (II) sulphate (0.005 mmol) were added sequentially. The reaction was stirred at room temperature for 11 h, TLC analysis indicated completion of reaction. The reaction mixture was concentrated under vacuum and extracted with EtOAc to give crude product. The crude was purified by column chromatography to afford pure product 6e (197 mg, 78%); mp: 147-149° C.; $^1$H NMR (300 MHz, CDCl$_3$) δ 10.17 (s, 1H), 8.24 (dd, J=4.9, 1.7 Hz, 1H), 7.55-7.48 (dd, J=7.7, 1.7 Hz, 1H), 7.17 (t, J=5.0 Hz, 1H), 6.87 (d, J=8.8 Hz, 2H), 6.62-6.57 (m, 1H), 6.42-6.39 (m, 3H), 5.42 (s, 2H), 4.66 (d, J=5.4 Hz, 2H), 3.79 (s, 3H), 3.75 ppm (s, 6H) MS (ESI m/z): 475 [M+H]$^+$. Yield: 78%

Example 20

N-((1-(3,5-Dimethoxybenzyl)-1H-1,2,3-triazol-4-yl) methyl)-2-(2,4-dimethoxyphenyl amino)nicotinamide (6g)

Compound 8 (194 mg, 1 mmol) and 2,4-dimethoxyaniline (9e, 153 mg, 1 mmol) were taken in ethylene glycol and heated at 140° C. for 6 h. Then the reaction mixture was cooled and extracted with ethyl acetate from the aqueous layer and concentrated in vacuum. The compound was further purified by column chromatography using 60-120 silica gel to obtain 2-(2,4-dimethoxyphenylamino)-N-(prop-2-ynyl) nicotinamide 10g as pure product. To a solution of 2-(2,4-dimethoxyphenylamino)-N-(prop-2-ynyl)nicotinamide (10 g, 150 mg, 0.48 mmol) and 1-(azidomethyl)-3,5-dimethoxybenzene (12d, 102 mg, 0.53 mmol) in 2:1 mixture of water and tert-butyl alcohol, sodium ascorbate (0.06 mmol) and copper (II) sulphate (0.005 mmol) were added sequentially. The reaction was stirred at room temperature for 12 h, TLC analysis indicated completion of reaction. The reaction mixture was concentrated under vacuum and extracted with EtOAc to give crude product. The crude was purified by column chromatography to afford pure product 6e (175 mg, 72%); mp: 147-149° C.; $^1$H NMR (500 MHz, CDCl$_3$) δ 10.36 (s, 1H), 8.25 (dd, J=5.0, 3.0 Hz, 1H), 7.73 (dd, J=7.0 Hz, 1H), 7.53 (s, 1H), 7.15 (brs, 1H), 6.58-6.54 (m, 1H), 6.47-6.43 (m, 2H), 6.36 (s, 3H), 5.41 (s, 2H), 4.66 (d, J=5.2 Hz, 2H), 3.91 (s, 3H), 3.80 (s, 3H), 3.74 ppm (s, 6H) MS (ESI m/z): 505 [M+H]$^+$. Yield: 72%

The compounds of present invention are obtained and the yield of compound of FORMULA 1 is ranging between 60-81%.

Examples for the preparation of compounds 2a, 2c, 2d, 2f, 2h, 2i, 2j, 2k, 3a-k, 4a-k, 5a, 5c, 5d, 5f, 5h, 5i, 5k, 6a, 6c, 6d, 6f, 6h, 6i, 6j and 6k.

| Compound no | Starting materials | Method of preparation |
|---|---|---|
| 2a | 2-(phenylamino)-N-(prop-2-ynyl)nicotinamide and 1-(azidomethyl)-4-fluorobenzene | As described in 1a. |
| 2c | 2-(4-chlorophenylamino)-N-(prop-2-ynyl)nicotinamide and 1-(azidomethyl)-4-fluorobenzene. | As described in 1c. |
| 2d | 2-(4-bromophenylamino)-N-(prop-2-ynyl)nicotinamide and 1-(azidomethyl)-4-fluorobenzene. | As described in 1d. |
| 2f | 2-(3-fluorophenylamino)-N-(prop-2-ynyl)nicotinamide and 1-(azidomethyl)-4-fluorobenzene | As described in 1f. |
| 2h | 2-(2,5-dimethoxyphenylamino)-N-(prop-2-ynyl)nicotinamide and 1-(azidomethyl)-4-fluorobenzene | As described in 1h. |
| 2i | 2-(3,5-dimethoxyphenylamino)-N-(prop-2-ynyl)nicotinamide and 1-(azidomethyl)-4-fluorobenzene | As described in 1i. |
| 2j | N-(prop-2-ynyl)-2-(3,4,5-trimethoxyphenylamino)nicotinamide and 1-(azidomethyl)-4-fluorobenzene | As described in 1j. |
| 2k | 2-(4-chlorobenzylamino)-N-(prop-2-ynyl)nicotinamide and 1-(azidomethyl)-4-fluorobenzene | As described in 1k. |
| 3a | 2-(phenylamino)-N-(prop-2-ynyl)nicotinamide and 1-(azidomethyl)-4-chlorobenzene | As described in 1a. |
| 3b | 2-(4-fluorophenylamino)-N-(prop-2-ynyl)nicotinamide and 1-(azidomethyl)-4-chlorobenzene. | As described in 1b. |
| 3c | 2-(4-chlorophenylamino)-N-(prop-2-ynyl)nicotinamide and 1-(azidomethyl)-4-chlorobenzene | As described in 1c. |
| 3d | 2-(4-bromophenylamino)-N-(prop-2-ynyl)nicotinamide and 1-(azidomethyl)-4-chlorobenzene | As described in 1d. |
| 3e | 2-(4-methoxyphenylamino)-N-(prop-2-ynyl)nicotinamide and 1-(azidomethyl)-4-chlorobenzene | As described in 1e. |
| 3f | 2-(3-fluorophenylamino)-N-(prop-2-ynyl)nicotinamide and 1-(azidomethyl)-4-chlorobenzene | As described in 1f. |
| 3g | 2-(2,4-dimethoxyphenylamino)-N-(prop-2-ynyl)nicotinamide and 1-(azidomethyl)-4-chlorobenzene | As described in 1g. |
| 3h | 2-(2,5-dimethoxyphenylamino)-N-(prop-2-ynyl)nicotinamide and 1-(azidomethyl)-4-chlorobenzene | As described in 1h. |
| 3i | 2-(3,5-dimethoxyphenylamino)-N-(prop-2-ynyl)nicotinamide and 1-(azidomethyl)-4-chlorobenzene | As described in 1i. |
| 3j | N-(prop-2-ynyl)-2-(3,4,5-trimethoxyphenylamino)nicotinamide and 1-(azidomethyl)-4-chlorobenzene | As described in 1j. |
| 3k | 2-(4-chlorobenzylamino)-N-(prop-2-ynyl)nicotinamide and 1-(azidomethyl)-4-chlorobenzene. | As described in 1k. |
| 4a | 2-(phenylamino)-N-(prop-2-ynyl)nicotinamide and 1-(azidomethyl)-4-bromobenzene | As described in 1a. |
| 4b | 2-(4-fluorophenylamino)-N-(prop-2-ynyl)nicotinamide and 1-(azidomethyl)-4-bromobenzene | As described in 1b. |
| 4c | 2-(4-chlorophenylamino)-N-(prop-2-ynyl)nicotinamide and 1-(azidomethyl)-4-bromobenzene | As described in 1c. |
| 4d | 2-(4-bromophenylamino)-N-(prop-2-ynyl)nicotinamide and 1-(azidomethyl)-4-bromobenzene | As described in 1d. |
| 4e | 2-(4-methoxyphenylamino)-N-(prop-2-ynyl)nicotinamide and 1-(azidomethyl)-4-bromobenzene | As described in 1e. |
| 4f | 2-(3-fluorophenylamino)-N-(prop-2-ynyl)nicotinamide and 1-(azidomethyl)-4-bromobenzene | As described in 1f. |
| 4g | 2-(2,4-dimethoxyphenylamino)-N-(prop-2-ynyl)nicotinamide and 1-(azidomethyl)-4-bromobenzene | As described in 1g. |
| 4h | 2-(2,5-dimethoxyphenylamino)-N-(prop-2-ynyl)nicotinamide and 1-(azidomethyl)-4-bromobenzene | As described in 1h. |
| 4i | 2-(3,5-dimethoxyphenylamino)-N-(prop-2-ynyl)nicotinamide and 1-(azidomethyl)-4-bromobenzene | As described in 1i. |
| 4j | N-(prop-2-ynyl)-2-(3,4,5-trimethoxyphenylamino)nicotinamide and 1-(azidomethyl)-4-bromobenzene | As described in 1j. |
| 4k | 2-(4-chlorobenzylamino)-N-(prop-2-ynyl)nicotinamide and 1-(azidomethyl)-4-bromobenzene | As described in 1k. |
| 5a | 2-(phenylamino)-N-(prop-2-ynyl)nicotinamide and 1-(azidomethyl)-4-methoxybenzene | As described in 1a. |
| 5c | 2-(4-chlorophenylamino)-N-(prop-2-ynyl)nicotinamide and 1-(azidomethyl)-4-methoxybenzene | As described in 1c. |
| 5d | 2-(4-bromophenylamino)-N-(prop-2-ynyl)nicotinamide and 1-(azidomethyl)-4-methoxybenzene | As described in 1d. |
| 5f | 2-(3-fluorophenylamino)-N-(prop-2-ynyl)nicotinamide and 1-(azidomethyl)-4-methoxybenzene | As described in 1f. |
| 5h | 2-(2,5-dimethoxyphenylamino)-N-(prop-2-ynyl)nicotinamide and 1-(azidomethyl)-4-methoxybenzene | As described in 1h. |
| 5i | 2-(3,5-dimethoxyphenylamino)-N-(prop-2-ynyl)nicotinamide and 1-(azidomethyl)-4-methoxybenzene | As described in 1i. |
| 5j | N-(prop-2-ynyl)-2-(3,4,5-trimethoxyphenylamino)nicotinamide and 1-(azidomethyl)-4-methoxybenzene | As described in 1j. |
| 5k | 2-(4-chlorobenzylamino)-N-(prop-2-ynyl)nicotinamide and and 1-(azidomethyl)-4-methoxybenzene | As described in 1k. |
| 6a | 2-(phenylamino)-N-(prop-2-ynyl)nicotinamide and 1-(azidomethyl)-3,5-dimethoxybenzene | As described in 1a. |
| 6c | 2-(4-chlorophenylamino)-N-(prop-2-ynyl)nicotinamide and 1-(azidomethyl)-3,5-dimethoxybenzene | As described in 1c. |
| 6d | 2-(4-bromophenylamino)-N-(prop-2-ynyl)nicotinamide and 1-(azidomethyl)-3,5-dimethoxybenzene | As described in 1d. |
| 6f | 2-(3-fluorophenylamino)-N-(prop-2-ynyl)nicotinamide and 1-(azidomethyl)-3,5-dimethoxybenzene | As described in 1f. |
| 6h | 2-(2,5-dimethoxyphenylamino)-N-(prop-2-ynyl)nicotinamide and 1-(azidomethyl)-3,5-dimethoxybenzene | As described in 1h |
| 6i | 2-(3,5-dimethoxyphenylamino)-N-(prop-2-ynyl)nicotinamide and 1-(azidomethyl)-3,5-dimethoxybenzene | As described in 1i. |
| 6j | N-(prop-2-ynyl)-2-(3,4,5-trimethoxyphenylamino)nicotinamide and 1-(azidomethyl)-3,5-dimethoxybenzene | As described in 1j. |
| 6k | 2-(4-chlorobenzylamino)-N-(prop-2-ynyl)nicotinamide and 1-(azidomethyl)-3,5-dimethoxybenzene | As described in 1k. |

Biological Activity:

The in vitro anticancer activity studies for these N-((1-benzyl-1H-1,2,3-triazol-4-yl)methyl) arylamide analogues were carried out at the National Cancer Institute, USA.

Anticancer Activity

The N-((1-benzyl-1H-1,2,3-triazol-4-yl)methyl)arylamide analogues have been tested at NCI, USA, against sixty human tumor cell lines derived from nine cancer types (leukemia, non-small cell lung cancer, colon cancer, CNS cancer, melanoma cancer, ovarian cancer, renal cancer, prostate cancer and breast cancer). For these compounds results are expressed as growth inhibition ($GI_{50}$) values as per NCI protocol. The anticancer activity data of compounds 1a, 1b, 1e, 1g, 1i and 1k are shown in Table 2.

TABLE 2

Cytotoxicity of compounds 1a, 1b, 1e, 1g, 1i and 1k in sixty cancer cell lines

| Cancer panel/ Cell lines | 1a | 1b | 1e | 1g | 1i | 1k |
|---|---|---|---|---|---|---|
| Leukemia | | | | | | |
| CCRF-CEM | 3.34 | NT | 3.80 | 1.20 | 4.19 | 3.05 |
| HL-60(TB) | 3.74 | NT | 2.66 | 2.21 | 3.97 | 3.39 |
| K-562 | 3.69 | NT | 3.48 | 0.75 | 4.34 | 3.24 |
| MOLT-4 | 3.74 | NT | 2.91 | 3.65 | 4.85 | 3.28 |
| RPMI-8226 | 3.61 | NT | 4.84 | 3.03 | 5.25 | 3.12 |
| SR | 2.56 | — | — | — | — | 3.31 |
| Non-small-cell-lung | | | | | | |
| A549/ATCC | 4.81 | 6.11 | 3.44 | 4.15 | 4.02 | 3.21 |
| EKVX | 5.18 | 25.3 | 4.16 | 5.09 | 6.33 | 3.65 |
| HOP-62 | 5.58 | 60.2 | 5.07 | 12.7 | 6.31 | 5.69 |
| HOP-92 | — | 10.7 | 5.67 | — | 4.67 | 4.23 |
| NCI-H226 | 3.24 | 38.6 | 3.92 | 2.24 | 9.82 | 3.66 |
| NCI-H23 | 3.73 | 29.9 | 3.45 | 2.24 | 6.22 | — |
| NCI-H322M | — | 5.29 | 5.24 | NT | 6.15 | — |
| NCI-H460 | 2.85 | 5.25 | 3.52 | 3.05 | 3.98 | 2.85 |
| NCI-H522 | 2.11 | 10.8 | 2.13 | 1.82 | 3.31 | 2.18 |
| Colon | | | | | | |
| COLO 205 | 2.79 | 6.22 | 2.86 | 2.14 | 4.12 | 2.18 |
| HCC-2998 | 3.70 | NT | 2.53 | 3.33 | 9.60 | 4.17 |
| HCT-116 | 3.40 | 5.02 | 4.17 | 3.08 | 4.34 | 3.18 |
| HCT-15 | 3.81 | — | 3.93 | 2.89 | 3.89 | 3.39 |
| HT29 | 3.65 | 5.60 | 3.66 | 3.26 | 3.88 | 2.96 |
| KM12 | 3.63 | 5.61 | 3.43 | 1.65 | 3.84 | 3.62 |
| SW-620 | 3.97 | 6.58 | 3.86 | 2.12 | 3.88 | 4.04 |
| CNS | | | | | | |
| SF-268 | 3.22 | 2.1 | 4.59 | 3.88 | 5.43 | 4.82 |
| SF-295 | 3.69 | 5.66 | 2.94 | 0.56 | 4.06 | 2.80 |
| SF-539 | 3.10 | 15.1 | 2.79 | 2.65 | 4.39 | 2.24 |
| SNB-19 | 3.27 | 20.7 | 3.55 | 3.33 | 9.64 | 3.91 |
| SNB-75 | 1.94 | 3.81 | 3.09 | 3.41 | 3.98 | 2.02 |
| U251 | 3.61 | 7.12 | 3.91 | 3.60 | 4.58 | 2.66 |
| Melanoma | | | | | | |
| LOX IMVI | 4.54 | 61.3 | 3.60 | 3.01 | 5.10 | 3.90 |
| MALME-3M | NT | 15.1 | 3.80 | 4.07 | 5.81 | 5.69 |
| M14 | 2.86 | 13.7 | 3.15 | 2.13 | 4.80 | 2.49 |
| MDA-MB-435 | 2.65 | 2.79 | 1.71 | 0.25 | 2.23 | 2.33 |
| SK-MEL-2 | 6.05 | 34.2 | 3.66 | 7.67 | 6.69 | 4.44 |
| SK-MEL-28 | 4.93 | 7.98 | 3.88 | 2.60 | 4.14 | 2.95 |
| SK-MEL-5 | 3.89 | 4.48 | 2.90 | 0.72 | 3.11 | 2.53 |
| UACC-257 | 1.42 | 6.87 | 4.82 | NT | 4.86 | 3.83 |
| UACC-62 | 3.02 | 6.51 | 3.13 | 1.43 | 3.86 | 2.08 |
| Ovarian | | | | | | |
| IGROV1 | 30.7 | 5.89 | NT | 5.96 | NT | 9.03 |
| OVCAR-3 | 17.7 | 2.98 | 3.69 | 1.54 | 3.69 | 3.48 |
| OVCAR-4 | 23.4 | 5.19 | 5.42 | 5.11 | 5.42 | 3.37 |
| OVCAR-5 | NT | 4.23 | 100 | 8.34 | 100 | 5.62 |
| OVCAR-8 | 7.44 | 3.72 | 5.96 | 4.10 | 5.96 | 3.63 |
| NCI/ADR-RES | 14.0 | 2.12 | 3.21 | 2.12 | 3.21 | 2.86 |
| SK-OV-3 | 5.94 | 3.11 | 4.33 | 2.59 | 4.33 | 3.32 |
| Renal | | | | | | |
| 786-0 | 23.2 | 5.59 | 6.73 | 4.06 | 6.73 | — |
| A498 | 13.7 | 2.35 | 4.18 | 1.01 | 4.18 | 2.12 |
| ACHN | 11.05 | 4.79 | 6.90 | 4.83 | 6.90 | 4.03 |
| CAKI-1 | 64.2 | 3.41 | 6.30 | 1.71 | 6.30 | 4.36 |
| SN12C | 52.9 | 4.75 | 7.41 | 1.71 | 7.41 | 3.44 |
| TK-10 | 24.5 | 4.59 | 5.16 | 3.14 | 5.16 | 3.70 |
| UO-31 | 86.3 | 3.00 | 5.25 | 8.06 | 5.25 | 3.00 |
| RXF 393 | 5.69 | 2.59 | 3.77 | 7.83 | 3.77 | 2.19 |
| Prostate | | | | | | |
| PC-3 | 20.4 | 3.86 | 4.74 | 0.62 | 4.74 | 2.96 |
| DU-145 | 8.58 | 3.76 | 1.05 | 3.37 | 1.05 | 4.00 |
| Breast | | | | | | |
| MCF7 | — | — | — | 0.65 | — | 2.99 |
| MDA-MB-31/ATCC | 14.5 | 3.09 | 5.35 | 5.54 | 5.35 | 2.29 |
| HS 578T | 30.9 | 5.90 | NT | 2.94 | NT | 2.72 |
| BT-549 | 45.5 | 4.58 | 7.16 | 3.51 | 7.16 | 2.72 |
| T-47D | 21.4 | 4.03 | 4.68 | 4.28 | 4.68 | 3.20 |
| MDA-MB-468 | 51.7 | 2.32 | 2.42 | 1.46 | 2.42 | 3.44 |

All the compounds showed enhanced antitumor activity in tested cell lines. In the present investigation, an attempt has been made, in view of the biological importance of both 2-anilino nicotinyl structure and 1,2,3-triazoles group. The resulting compounds 1a, 1b, 1c, 1d, 1f, 1g, 1i, 1k, 6b and 6g were found to be more potent with $IC_{50}$ values ranging from 1.25-3.98 and 0.74-2.51 μM and compared with E7010 $IC_{50}$ values 4.45 and 9.06 μM against A549 and MCF-7 cell lines respectively (*Chem MedChem* 2012, 7, 680-693). Introduction of triazole group on 2-anilino nicotinyl moiety resulted that there is enhancement of biological activity of representative compounds (1a, 1b, 1c, 1d, 1f, 1g, 1i, 1k, 6b and 6g) compare with E7010. Biological data of representative compounds has been provided in Table 1.

(Novel sulfonamides as potential, systemically active antitumor agents. Yoshino, H.; Ueda, N.; Niijima, J.; Sugumi, H.; Kotake, Y.; Koyanagi, N.; Yoshimatsu, K.; Asada, M.; Watanabe, T.; Nagasu, T. *J. Med. Chem.* 1992, 35, 2496-2497)

TABLE 3

$IC_{50}$ (μM) values of compounds and E7010

| Compound no | A549 | MCF-7 |
|---|---|---|
| 1a | 1.54 | 1.65 |
| 1b | 1.69 | 1.65 |
| 1c | 3.98 | 2.51 |
| 1d | 1.90 | 0.97 |
| 1f | 1.90 | 1.78 |
| 1g | 1.57 | 0.74 |
| 1i | 1.93 | 0.93 |
| 1k | 1.79 | 2.51 |
| 6b | 1.25 | 1.0 |
| 6g | 1.31 | 1.17 |
| E7010 | 4.45 | 9.06 |

Significance of the Work Carried Out

A compound of formula 1 that has been synthesized exhibited significant cytotoxic activity against different human tumour cell lines.

Advantages of the Invention

1. The present invention provides N-((1-Benzyl-1H-1,2,3-triazol-4-yl)methyl)arylamides as potential antitumor agents.
2. It also provides a process for the preparation of novel N-((1-Benzyl-1H-1,2,3-triazol-4-yl)methyl)arylamides.

We claim:
1. A compound of formula 1,

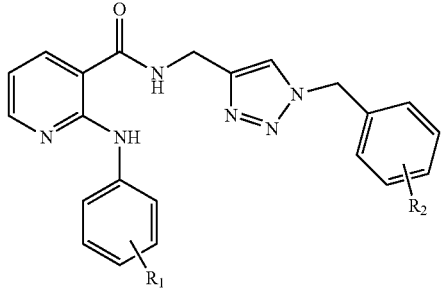

Formula 1 wherein
R1 is hydrogen, halogen, 2,4-diOMe, 2,5-diOMe, 3,5-diOMe, or 3,4,5-triOMe; and
R2 is halogen, 3-OPh, 4-OMe, or 3,5-diOMe.

2. The compound of formula 1 as claimed in claim 1, wherein R1 is halogen and the halogen is selected from the group consisting of chlorine, bromine, and fluorine.

3. The compound formula 1 as claimed in claim 1, wherein R1 is 2,4-diOMe, 2,5-diOMe, 3,5-diOMe, or 3,4,5-triOMe.

4. The compound of formula 1 as claimed in claim 1, wherein R2 is halogen and the halogen is selected from the group consisting of chlorine, bromine and fluorine.

5. The compound of formula 1 as claimed in claim 1, wherein the R2 is 3-OPh, 4-OMe, or 3,5-diOMe.

6. The compound formula 1 as claimed in claim 1, selected from the group consisting of:
N-((1-(3-Phenoxybenzyl)-1H-1,2,3-triazol-4-yl)methyl)-2-(phenylamino)nicotinamide (1a);
2-(4-Fluorophenylamino)-N-((1-(3-phenoxybenzyl)-1H-1,2,3-triazol4-yl)methyl)nicotinamide (1b);
2-(4-Chlorophenylamino)-N-((1-(3-phenoxybenzyl)-1H-1,2,3-triazol-4-yl)methyl)nicotinamide (1c);
2-(4-Bromophenylamino)-N-((1-(3-phenoxybenzyl)-1H-1,2,3-triazol-4-yl)methyl)nicotinamide (1d);
2-(4-Methoxyphenylamino)-N-((1-(3-phenoxybenzyl)-1H-1,2,3-triazol-4-yl)methyl) nicotinamide (1e);
2-(3-Fluorophenylamino)-N-((1-(3-phenoxybenzyl)-1H-1,2,3-triazol-4-yl)methyl)nicotinamide (1f);
2-(2,4-Dimethoxyphenylamino)-N-((1-(3-phenoxybenzyl)-1H-1,2,3-triazol-4-yl)methyl)nicotinamide (1g);
2-(2,5-Dimethoxyphenylamino)-N-((1-(3-phenoxybenzyl)-1H-1,2,3-triazol-4-yl)methyl)nicotinamide (1h);
2-(3,5-Dimethoxyphenylamino)-N-((1-(3-phenoxybenzyl)-1H-1,2,3-triazol-4-yl)methyl)nicotinamide (1i);
N-((1-(3-Phenoxybenzyl)-1H-1,2,3-triazol-4-yl)methyl)-2-(3,4,5-trimethoxyphenylamino)nicotinamide (1j);
2-(4-Chlorobenzylamino)-N-((1-(3-phenoxybenzyl)-1H-1,2,3-triazol-4-yl)methyl)nicotinamide (1k);
N-((1-(4-Fluorobenzyl)-1H-1,2,3-triazol-4-yl)methyl)-2-(phenylamino)nicotinamide (2a);
N-((1-(4-Fluorobenzyl)-1H-1,2,3-triazol-4-yl)methyl)-2-((4-fluorophenyl)amino)nicotinamide (2b);
2-((4-Chlorophenyl)amino)-N-((1-(4-fluorobenzyl)-1H-1,2,3-triazol-4-yl)methyl)nicotinamide (2c);
2-((4-Bromophenyl)amino)-N-((1-(4-fluorobenzyl)-1H-1,2,3-triazol-4-yl)methyl)nicotinamide (2d);
N-((1-(4-Fluorobenzyl)-1H-1,2,3-triazol-4-yl)methyl)-2-((4-methoxyphenyl)amino)nicotinamide (2e);
N-((1-(4-Fluorobenzyl)-1H-1,2,3-triazol-4-yl)methyl)-2-((3-fluorophenyl)amino)nicotinamide (2f);
2-((2,4-Dimethoxyphenyl)amino)-N-((1-(4-fluorobenzyl)-1H-1,2,3-triazol-4-yl)methyl)nicotinamide (2g);
2-((2,5-Dimethoxyphenyl)amino)-N-((1-(4-fluorobenzyl)-1H-1,2,3-triazol-4-yl)methyl)nicotinamide (2h);
2-((3,5-Dimethoxyphenyl)amino)-N-((1-(4-fluorobenzyl)-1H-1,2,3-triazol-4-yl)methyl)nicotinamide (2i);
N-((1-(4-Fluorobenzyl)-1H-1,2,3-triazol-4-yl)methyl)-2-((3,4,5-trimethoxyphenyl)amino)nicotinamide (2j);
2-(4-Chlorobenzylamino)-N-((1-(4-fluorobenzyl)-1H-1,2,3-triazol-4-yl)methyl)nicotinamide (2k);
N-((1-(4-Chlorobenzyl)-1H-1,2,3-triazol-4-yl)methyl)-2-(phenylamino)nicotinamide (3a);
N-((1-(4-Chlorobenzyl)-1H-1,2,3-triazol-4-yl)methyl)-2-((4-fluorophenyl)amino)nicotinamide (3b);
N-((1-(4-Chlorobenzyl)-1H-1,2,3-triazol-4-yl)methyl)-2-((4-chlorophenyl)amino)nicotinamide (3c);
2-((4-Bromophenyl)amino)-N-((1-(4-chlorobenzyl)-1H-1,2,3-triazol-4-yl)methyl)nicotinamide (3d);
N-((1-(4-Bromobenzyl)-1H-1,2,3-triazol-4-yl)methyl)-2-((4-methoxyphenyl)amino)nicotinamide (3e));
N-((1-(4-Chlorobenzyl)-1H-1,2,3-triazol-4-yl)methyl)-2-((3-fluorophenyl)amino)nicotinamide (3f);
N-((1-(4-Chlorobenzyl)-1H-1,2,3-triazol-4-yl)methyl)-2-((2,4-dimethoxyphenyl)amino)nicotinamide (3g);
N-((1-(4-Chlorobenzyl)-1H-1,2,3-triazol-4-yl)methyl)-2-((2,5-dimethoxyphenyl)amino)nicotinamide (3h);
N-((1-(4-Bromobenzyl)-1H-1,2,3-triazol-4-yl)methyl)-2-((3,5-dimethoxyphenyl)amino)nicotinamide (3i);
N-((1-(4-Chlorobenzyl)-1H-1,2,3-triazol-4-yl)methyl)-2-((3,4,5-trimethoxyphenyl)amino)nicotinamide (3j);
N-((1-(4-Chlorobenzyl)-1H-1,2,3-triazol-4-yl)methyl)-2-((4-chlorobenzyl)amino)nicotinamide (3k);
N-((1-(4-Bromobenzyl)-1H-1,2,3-triazol-4-yl)methyl)-2-(phenylamino)nicotinamide (4a);
N-((1-(4-Bromobenzyl)-1H-1,2,3-triazol-4-yl)methyl)-2-((4-fluorophenyl)amino) nicotinamide (4b);
N-((1-(4-Bromobenzyl)-1H-1,2,3-triazol-4-yl)methyl)-2-((4-chlorphenyl)amino) nicotinamide (4c);
N-((1-(4-Bromobenzyl)-1H-1,2,3-triazol-4-yl)methyl)-2-((4-bromophenyl)amino) nicotinamide (4d);
N-((1-(4-Bromobenzyl)-1H-1,2,3-triazol-4-yl)methyl)-2-((4-methoxyphenyl)amino) nicotinamide (4e);
N-((1-(4-Bromobenzyl)-H-1,2,3-triazol-4-yl)methyl)-2-((3-fluorophenyl)amino) nicotinamide (4f);
N-((1-(4-Bromobenzyl)-H-1,2,3-triazol-4-yl)methyl)-2-((2,4-dimethoxyphenyl)amino)nicotinamide (4g);
N-((1-(4-Bromobenzyl)-1H-1,2,3-triazol-4-yl)methyl)-2-((2,5-dimethoxyphenyl)amino)nicotinamide (4h);
N-((1-(4-Bromobenzyl)-1H-1,2,3-triazol-4-yl)methyl)-2-((3,5-dimethoxyphenyl)amino)nicotinamide (4i);
N-((1-(4-Bromobenzyl)-1H-1,2,3-triazol-4-yl)methyl)-2-((3,4,5-trimethoxyphenyl)amino)nicotinamide (4j);
N-((1-(4-Bromobenzyl)-1H-1,2,3-triazol-4-yl)methyl)-2-((4-chlorobenzyl)amino)nicotinamide (4k);
N-((1-(4-Methoxybenzyl)-1H-1,2,3-triazol-4-yl)methyl)-2-(phenylamino)nicotinamide (5a);
2-((4-Fluorophenyl)amino)-N-((1-(4-methoxybenzyl)-1H-1,2,3-triazol-4-yl)methyl)nicotinamide (5b);
2-((4-Chlorophenyl)amino)-N-((1-(4-methoxybenzyl)-1H-1,2,3-triazol-4-yl)methyl)nicotinamide (5c);
2-((4-Bromophenyl)amino)-N-((1-(4-methoxybenzyl)-1H-1,2,3-triazol-4-yl)methyl)nicotinamide (5d);
N-((1-(4-Methoxybenzyl)-1H-1,2,3-triazol-4-yl)methyl)-2-((4-methoxyphenyl)amino) nicotinamide (5e);
2-((3-Fluorophenyl)amino)-N-((1-(4-methoxybenzyl)-1H-1,2,3-triazol-4-yl)methyl)nicotinamide (5f);
2-((2,4-Dimethoxyphenyl)amino)-N-((1-(4-methoxybenzyl)-1H-1,2,3-triazol-4-yl)methyl)nicotinamide (5g);

2-((2,5-Dimethoxyphenyl)amino)-N-((1-(4-methoxybenzyl)-1H-1,2,3-triazol-4-yl)methyl)nicotinamide (5h);
2-((3,5-Dimethoxyphenyl)amino)-N-((1-(4-methoxybenzyl)-1H-1,2,3-triazol-4-yl)methyl)nicotinamide (5i);
N-((1-(4-Methoxybenzyl)-1H-1,2,3-triazol-4-yl)methyl)-2-((3,4,5-trimethoxyphenyl)amino)nicotinamide (5j);
N-((1-(4-Methoxybenzyl)-1H-1,2,3-triazol-4-yl)methyl)-2-((3,4,5-trimethoxyphenyl)amino)nicotinamide (5k);
N-((1-(3,5-Dimethoxybenzyl)-1H-1,2,3-triazol-4-yl)methyl)-2-(phenylamino)nicotinamide (6a);
N-((1-(3,5-Dimethoxybenzyl)-1H-1,2,3-triazol-4-yl)methyl)-2-((4-fluorophenyl)amino)nicotinamide (6b);
2-((4-Chlorophenyl)amino)-N-((1-(3,5-dimethoxybenzyl)-1H-1,2,3-triazol-4-yl)methyl)nicotinamide (6c);
2-((4-Bromophenyl)amino)-N-((1-(3,5-dimethoxybenzyl)-1H-1,2,3-triazol-4-yl)methyl)nicotinamide (6d);
N-((1-(3,5-Dimethoxybenzyl)-1H-1,2,3-triazol-4-yl)methyl)-2-((4-methoxyphenyl)amino)nicotinamide (6e);
N-((1-(3,5-Dimethoxybenzyl)-1H-1,2,3-triazol-4-yl)methyl)-2-((3-fluorophenyl)amino)nicotinamide (6f);
N-((1-(3,5-Dimethoxybenzyl)-1H-1,2,3-triazol-4-yl)methyl)-2-((2,4-dimethoxyphenyl)amino)nicotinamide (6g);
N-((1-(3,5-Dimethoxybenzyl)-1H-1,2,3-triazol-4-yl)methyl)-2-((2,5-dimethoxyphenyl)amino)nicotinamide (6h);
N-((1-(3,5-Dimethoxybenzyl)-1H-1,2,3-triazol-4-yl)methyl)-2-((3,5-dimethoxyphenyl)amino)nicotinamide (6i);
N-((1-(3,5-Dimethoxybenzyl)-1H-1,2,3-triazol-4-yl)methyl)-2-((3,4,5-trimethoxyphenyl)amino)nicotinamide (6j); and
2-((4-Chlorobenzyl)amino)-N-((1-(3,5-dimethoxybenzyl)-1H-1,2,3-triazol-4-yl)methyl)nicotinamide (6k).

7. A method of inhibiting growth of tumor cells, comprising contacting tumor cells with a compound of formula 1 as claimed in claim 1.

8. A process for the preparation of compound of formula 1 as claimed in claim 1, comprising the steps:
i. reacting compound of formula 8

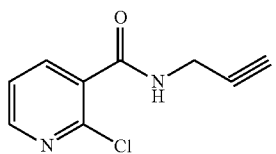

8 with compound of formula 9a-k

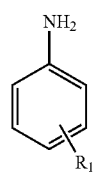

9a-k in ethylene glycol at a temperature ranging between 130-140° C. for a time period ranging between 5-6 hr to obtain substituted nicotinamide of formula 10a-k,

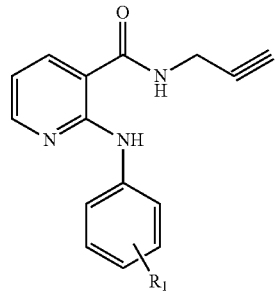

10a-k ii. reacting substituted nicotinamide of formula 10a-k as obtained in step (i) with substituted azides of formula 12a-k

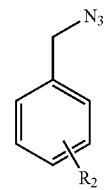

12a-k in a mixture of water and tert-butyl alcohol in the ratio of 2:1 followed by sequential addition of sodium ascorbate and copper sulphate at a temperature ranging between 25-30° C. for a time period ranging between 10-12 h to obtain compound of formula 1.

9. The process as claimed in claim 8, wherein the compound 9 a-k used in step (i) is selected from the group consisting of Aniline, 4-fluoroaniline, 4-bromoaniline, 4 methoxyaniline, 3-fluoroaniline, 2,4-dimethoxyaniline, 2,5-dimethoxyaniline, 3,5-dimethoxyaniline, 3,4,5-trimethoxyaniline and (4-chlorophenyl)methanamine.

10. The process as claimed in claim 8, wherein the substituted nicotinamide of formula 10 a-k used in step (ii) is selected from the group consisting of 2-(phenylamino)-N-(prop-2-ynyl)nicotinamide, 2-(4-fluorophenylamino)-N-(prop-2-ynyl)nicotinamide, 2-(4-chlorophenylamino)-N-(prop-2-ynyl)nicotinamide, 2-(4-bromophenylamino)-N-(prop-2-ynyl)nicotinamide, 2-(4-methoxyphenylamino)-N-(prop-2-ynyl)nicotinamide, 2-(3-fluorophenylamino)-N-(prop-2-ynyl)nicotinamide, 2-(2,4-dimethoxyphenylamino)-N-(prop-2-ynyl)nicotinamide, 2-(2,5-dimethoxyphenylamino)-N-(prop-2-ynyl)nicotinamide, 2-(3,5-dimethoxyphenylamino)-N-(prop-2-ynyl)nicotinamide, N-(prop-2-ynyl)-2-(3,4,5-trimethoxyphenylamino) nicotinamide and 2-(4-chlorobenzylamino)-N-(prop-2-ynyl) nicotinamide.

11. The process as claimed in claim 8, wherein the substituted benzylazide of formula 12a-k used in step (ii) is selected from the group consisting of 1-(azidomethyl)-3-phenoxybenzene, 1-(azidomethyl)-4-fluorobenzene, 1-(azidomethyl)-4-chlorobenzene, 1-(azidomethyl)-4-bromobenzene, 1-(azidomethyl)-4-methoxybenzene and 1-(azidomethyl)-3,5-dimethoxybenzene.

12. The method of claim 7, wherein the tumor cells are leukemia cells.

13. The method of claim 7, wherein the tumor cells are non-small cell lung cancer cells.

14. The method of claim 7, wherein the tumor cells are colon cancer cells.

15. The method of claim 7, wherein the tumor cells are central nervous system (CNS) cancer cells.

16. The method of claim 7, wherein the tumor cells are melanoma cells.

17. The method of claim 7, wherein the tumor cells are ovarian cancer cells.

18. The method of claim 7, wherein the tumor cells are renal cancer cells.

19. The method of claim 7, wherein the tumor cells are prostate cancer cells.

20. The method of claim 7, wherein the tumor cells are breast cancer cells.

* * * * *